United States Patent
Schneider et al.

(10) Patent No.: US 10,874,749 B2
(45) Date of Patent: Dec. 29, 2020

(54) GENE THERAPIES FOR NEURODEGENERATIVE DISORDERS TARGETING GANGLIOSIDE BIOSYNTHETIC PATHWAYS

(71) Applicant: THOMAS JEFFERSON UNIVERSITY, Philadelphia, PA (US)

(72) Inventors: Jay S. Schneider, Cherry Hill, NJ (US); David W. Anderson, Newtown Square, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 15/746,355

(22) PCT Filed: Jul. 21, 2016

(86) PCT No.: PCT/US2016/043393
§ 371 (c)(1),
(2) Date: Jan. 19, 2018

(87) PCT Pub. No.: WO2017/015491
PCT Pub. Date: Jan. 26, 2017

(65) Prior Publication Data
US 2018/0214573 A1    Aug. 2, 2018

Related U.S. Application Data

(60) Provisional application No. 62/194,954, filed on Jul. 21, 2015, provisional application No. 62/194,910, filed on Jul. 21, 2015.

(51) Int. Cl.
| | |
|---|---|
| *A61K 48/00* | (2006.01) |
| *A61K 35/30* | (2015.01) |
| *C12N 15/113* | (2010.01) |
| *C12Q 1/6883* | (2018.01) |
| *A61K 45/06* | (2006.01) |
| *C12Q 1/68* | (2018.01) |
| *A61K 31/7088* | (2006.01) |
| *C12N 15/85* | (2006.01) |

(52) U.S. Cl.
CPC ........ *A61K 48/005* (2013.01); *A61K 31/7088* (2013.01); *A61K 35/30* (2013.01); *A61K 45/06* (2013.01); *A61K 48/0033* (2013.01); *A61K 48/0075* (2013.01); *C12N 15/1137* (2013.01); *C12N 15/85* (2013.01); *C12Q 1/68* (2013.01); *C12Q 1/6883* (2013.01); *C12Y 204/99004* (2013.01); *A01K 2207/20* (2013.01); *A01K 2227/105* (2013.01); *A01K 2267/0318* (2013.01); *A61K 48/0058* (2013.01); *C12N 2015/8518* (2013.01); *C12N 2310/531* (2013.01); *C12N 2320/31* (2013.01); *C12N 2750/14143* (2013.01); *C12Q 2600/158* (2013.01)

(58) Field of Classification Search
CPC ..................................................... A61K 48/005
See application file for complete search history.

(56) References Cited

U.S. PATENT DOCUMENTS

| | | | |
|---|---|---|---|
| 9,023,812 B2 * | 5/2015 | Sipione | A61K 31/7032 514/25 |
| 2002/0132293 A1 | 9/2002 | Palm et al. | |
| 2003/0031681 A1 * | 2/2003 | McCart | C12N 15/86 424/186.1 |
| 2004/0076613 A1 * | 4/2004 | Mazarakis | A61K 38/185 424/93.2 |
| 2009/0142327 A1 | 6/2009 | Fang et al. | |

FOREIGN PATENT DOCUMENTS

WO     2011026216 A1    3/2011

OTHER PUBLICATIONS

Furukawa et al. ((online Jul. 18, 2014) "Glycosphingolipids in the Regulation of the Nervous System." In: Yu R., Schengrund CL. (eds) Glycobiology of the Nervous System. Advances in Neurobiology, vol. 9. Springer, New York, NY). (Year: 2014).*
Mendez-Otero et al. ((2013) Role of Gangliosides in Neurological Development and the Influence of Dietary Sources. In: Watson R., Grimble G., Preedy V., Zibadi S. (eds) Nutrition in Infancy. Nutrition and Health. Humana Press, Totowa, NJ) (Year: 2013).*
Kappagantula et al. (The Journal of Neuroscience. Feb. 12, 2014. 34(7): 2477-2492). (Year: 2014).*
JS Schneider ((2013) Advances in Neurobiology Dec. 31, 2013. 9:449-461). (Year: 2013).*

(Continued)

*Primary Examiner* — Scott Long
(74) *Attorney, Agent, or Firm* — Saul Ewing Arnstein & Lehr LLP; Kathryn Doyle; Justin Crotty

(57) ABSTRACT

A composition of matter comprising an adeno-associated virus (AAV) or other human compatible virus, encoding the gene for Sialidase Neu3, B3Galt4, St3Gal2, or combinations thereof, and a neuron specific promoter, wherein the composition is suitable for administration to a patient comprising injecting the AAV or other human compatible virus into the brain by intracranial stereotaxic injunction; wherein the AAV's encoding for the Sialidase Neu3, B3Galt4, St3Gal2, or combinations thereof enhance and/or normalize levels of GM1 in neurons, providing both therapeutic relief and disease modifying effects in specific areas of the brain relevant to particular neurodegenerative diseases.

14 Claims, 24 Drawing Sheets

(56) References Cited

OTHER PUBLICATIONS

Hioki, H et al. "Efficient Gene Transduction of Neurons by Lentivirus with Enhaced Neuron-Specific Promoters". Gene Therapy. Mar. 15, 2007; vol. 14, No. 11; pp. 872-882.
Wang, L et al. Gangliosides GD1a Suppresses TNFalpha Expression via Pkn1 at the Transcriptional Level in Mouse Osteosarcoma-Derived FBJ Cells. Biochemical and Biophysical Research Communications. Apr. 22, 2008; vol. 371, No. 2; pp. 230-235.
Monti, E et al. Identification and Expression of NEU3, a Novel Human Sialidase associated to the Plasma Membrane. The Biochemical Jounral. Jul. 1, 2009; vol. 349, No. 1; pp. 343-351.
Haves, EPD et al. "Sphingolipids and Gangliosides of the Nervous System in Membrane Function and Dysfunction". FEBS Letters. Dec. 17, 2009 vol. 584, No. 9; pp. 1748-1759; DOI: 101.1016/j.febslet.2009.12.010.
Lowery, R et al. "Intracranial Injection of Adeno-associated Viral Vectors". Journal of Visualized Experiments. Nov. 17, 2010; vol. 45, No. 2140; pp. 1-3; DOI: 10.3791/2140.
Palmano, K et al. "The Role of Gangliosides in Neurodevelopment". Nutrients. May 22, 2015; vol. 7 , No. 5; pp. 3891-3913; DOI: 10.3390/nu7053891.
Schneider, JS et al. GM1 Ganglioside in Parkinson's Disease: Pilot Study of Effects on Dopamine Transporter Binding. Journal of the Neurological Sciences. Jun. 16, 2015; vol. 356, No. 1-2; pp. 1-18; DOI: 10.1016/j.ins.2015.06.028.
International Search Report dated Nov. 8, 2016 of International Patent Application No. PCT/US2016/043393.
Bates, et al., "Huntington disease", Nature Review, Disease Primers; 1, 2015, 1-21.
Chiavegatto , et al., "A Functional Role for Complex Gangliosides: Motor Deficits in GM2/GD2 Synthase Knockout Mice", Experimental Neurology; 166, 2000, 227-234.
Furukawa, K. , "B3-Galactosyltransferase-IV (GM1 Synthase)", Handbook of Glyctosyltransferases and Related Genes. Tokyo, Springer Japan:, 2002, 33-36.
Kozireski-Chuback , et al., "Axonogenesis in Neuro-2a Cells Correlates With GM1 Upregulation in the Nuclear and Plasma Membranes", Journal of Neuroscience Research, 57, 1999, 541-550.
Liu , et al., "A genetic model of substrate deprivation therapy for a glycosphingolipid storage disorder", The Journal of Clinical Investigation; 103(4), 1999, 497-505.
Cai , et al., "Improved tools for the Brainbow toolbox", Nature Methods, May 2013.
Iacovitti , et al., "A protocol for the differentiation of human embryonic stem cells into dopaminergic neurons using only chemically defined human additives: Studies in vitro and in vivo", Brain Research, vol. 1127, Jan. 2007, 19-25.
Kidd and Schneider , et al., "Protective Effects of Valproic Acid on the Nigrostriatal Dopamine System in an MPTP Mouse Model of Parkinson's Disease", Neuroscience; 194, Oct. 2011, 189-194.

\* cited by examiner

Dopamine Uptake Study

Pump Implanted — Tissue Collection

Day 0 — 7 — 12

B3Galt4 siRNA Decreases GM1 Expression in SK-N-SH Cells

NT  siRNA

Neuroprotection in an MPTP Mouse PD Model

GENE THERAPIES FOR NEURODEGENERATIVE DISORDERS TARGETING GANGLIOSIDE BIOSYNTHETIC PATHWAYS

CROSS REFERENCE TO RELATED APPLICATIONS

This application is a National Phase under 35 U.S.C. 371 of International Application No. PCT/US16/43393, filed Jul. 21, 2016, which claims the benefit of U.S. Provisional Application Ser. No. 62/194,910, filed Jul. 21, 2015 and 62/194,954, filed Jul. 21, 2015, the disclosure contents of which are hereby incorporated by reference in their entirety.

FIELD OF INVENTION

The present application is generally related to therapeutic treatments for neurodegerative disorders including Parkinson's disease (PD) and Huntington's disease (HD) comprising administration of a Sialidase Neu3 through gene therapy, through administration of B3Galt4 cDNA or a combination thereof, to a patient suffering from a neurodegenerative disease.

BACKGROUND OF THE INVENTION

HD is a hereditary autosomal-dominant, progressive neurodegenerative disorder, resulting from expansion of a polygultamine (CAG) repeat in the gene coding for the Huntingtin (Htt) protein, leading to formation of mutant Htt (mHtt), which confers a toxic gain of function, with neurons of the striatum being particularly vulnerable. Accumulation of mHtt drives neuronal dysfunction via transcriptional dysregulation, modification of cell signaling, abnormal axonal transport and synaptic activity leading to clinical signs and symptoms including chorea, dystonia, incoordination, cognitive decline and behavioral difficulties, culminating with death. Latency from diagnosis to death is typically approximately 20 years. Death is commonly due to complications of falling and/or dysphagia and aspiration, although it is estimated that >25% of patients attempt suicide at some point after diagnosis.

While genetic testing is available for HD, less than 5% of at-risk individuals elect to have predictive testing, with many citing the lack of an effective treatment as the rational for this decision. Currently the standard of care for HD is symptomatic, utilizing modestly effective anti-choreic drugs such as tetrabenazine. The use of symptomatic therapy does not alter the course of the disease. Survival rates in treated v. untreated patients are similar. As such, there is a significant unmet medical need for an effective, disease modifying therapy for HD.

Recent research found that as well as the mHtt toxicity in striatal (and cortical) neurons in HD, there is a significant dysregulation of ganglioside biosynthesis in these cells in HD models. Similar defects were found in fibroblasts from HD patients, suggesting that dysregulation in ganglioside expression may be a universal phenomenon in HD. Gangliosides, sialic acid containing sphingolipids, are major components of membrane lipid rafts where they act as modulators of cell signaling. Found throughout the body, gangliosides are highly enriched in the central nervous system (CNS), where they are critical to normal CNS development and neuron survival. Maglione et al. described impaired ganglioside metabolism in tissues from HD patients (fibroblasts and brain) and in a transgenic model of HD in mice (YAC128). These findings have been confirmed by others and extended to the R6/1 transgenic HD mouse, further strengthening the correlation between ganglioside dysregulation and HD. Primarily, the monosialoganglioside (GM1) is significantly reduced in both HD and PDmodels, although downstream polysialogangliosides such as GD1a, GD1b, GT1b are also partially affected. The administration of bovine brain-derived GM1 by infusion pump to YAC128 mice that were symptomatic for motor impairment resulted in normalization of motor function within 2 weeks of the start of treatment and lasting until the last day of infusion and resulted in phosphorylation of mHtt at serine residues 13 and 16 that attenuated mHtt toxicity, suggesting a disease modifying effect of GM1 administration.

Parkinson's disease is another neurodegenerative disorder that slowly progresses and is characterized by loss of dopamine-producing neurons in the substantia nigra, loss of forebrain dopamine, and a time-dependent worsening of clinical symptoms. Although symptomatic improvement can be obtained with available pharmacotherapies, functional ability deteriorates over time with the progressive loss of nigrostriatal dopamine neurons. Development of therapies that can slow the progression of the disease would fill a major unmet medical need in PD.

It is estimated that PD is the second most common neurodegenerative disease of mid to late life, with estimates of 1 of every 200 persons in the US aged 60-69 having PD. Additionally, 1 in 100 persons over 70 and 1 in every 35 persons over 80 suffer from PD. Worldwide, numbers suggest that between 4 to 5 million people suffer from PD and that number could double to between 8-10 million by 2030.

Current gold-standard treatment for PD is a drug first discovered in the 1960's, levodopa, which strictly provides symptomatic relief. New therapies are needed to provide symptomatic relief and protection against continued neuronal degeneration to those who suffer from neurodegenerative diseases such as PD.

As in HD, there are decreased levels of GM1 in the PD brain (particularly in the substantia nigra) and administration of bovine brain-derived GM1 is neuroprotective in animal and cell models of PD and has both symptomatic effects and slows disease progression in PD patients. However, due to drawbacks associated with the administration of animal brain-derived GM1, including the low ability of systemically administered GM1 to gain access to the brain, there is a need for new methods of treatment for increasing GM1 levels in the brain.

SUMMARY OF THE INVENTION

In accordance with these and other objects, a first embodiment of an invention disclosed herein is directed to a composition of matter comprising a viral vector expressing an exogenous nucleic acid sequence comprising a functional sialidase Neu3 enzyme and a promoter operably linked to said nucleic acid sequence. Said composition can suitably be utilized for treatment of neurodegenerative diseases or disorders to modify the amounts of GM1 in the brain.

A method of increasing the amount of GM1 in a brain tissue comprising administering to a patient an effective amount of an AAV encoding for sialidase Neu3, to the patient, wherein the sialidase Neu3 is effective in increasing the amounts of GM1 in the brain tissue of interest.

A method of increasing the amount of GM1 in a brain tissue comprising a concomitant treatment of GM1 and gene therapy comprising an AAV encoding for sialidase Neu3, wherein the GM1 is administered to directly increase GM1 levels in the brain and the AAV is administered to upregulate the production of GM1 through modification of the sialidase Neu3 so as to modify and stabilize the levels of GM1 in the brain; and wherein the levels of GM1 in the brain are thereafter increased as compared to the levels prior to administration.

A further embodiment is directed to a method of increasing the amount of GM1 in a brain tissue comprising a first step of administering an effective amount of an AAV encoding for sialidase Neu3 to a patient followed by a concomitant therapy comprising administration of an AAV to administer a gene encoding for B3Galt4. Based on experimental data, the gene encoding St3Gal2 (which converts GM1 to GD1a and GD1b to GT1b) is also downregulated in HD models and HD fibroblasts. Furthermore, there is some evidence that St3Gal2 is also downregulated in PD. Therefore, an appropriate AAV to administer St3Gal2 can also be utilized to increase levels of GD1a and GT1b which could then be converted into GM1 via AAV Neu3.

A further embodiment is directed to a method for treating a neurodegenerative disease or condition comprising administering an effective amount of a human compatible engineered adeno-associated virus (AAV) or lentivirus containing the B3Galt4 sequence under the control of neuronal specific promoters administered to the patient with a neurodegenerative disease or condition by intracranial stereotaxic injunction or by systemic administration.

A further embodiment is directed to a method to increase endogenous GM1 ganglioside in the substantia nigra in a PD patient or in the caudate nucleus, the putamen and/or additional affected brain regions in an HD patient, by administering an effective amount of a composition encoding for Neu3, and optional concomitant administration of shRNA or siRNA directed against St3gal2 to increase GM1 levels. Through administration of a Neu3-based therapy, it would be an advantage to try to increase GD1a and GT1b which are substrates for Neu3 and will help to allow more GM1 to be made.

A further embodiment is directed to a method for increasing GM1 levels in a patient suffering from a neurodegenerative disease or condition comprising administering to said patient an effective amount of an shRNA or siRNA for St3gal2, sufficient to increase GM1 levels in said patient with a concomitant therapy comprising administration of B3Galt4 cDNA to said patient.

A further embodiment is directed to a method to increase endogenous GM1 ganglioside in the brain comprising administering GM1 directly to a patient suffering from a neurodegenerative disease and administering B3Galt4 cDNA to increase production of GM1 in the brain; wherein the direct administration provides direct increase of GM1 in the brain and the B3Galt4 cDNA provides protective and restorative effects by modulating and increasing the native production of GM1 in the brain.

A further embodiment is directed to a method to increase endogenous GM1 ganglioside in the brain comprising administering GM1 directly to a patient suffering from a neurodegenerative disease or condition and administering B3Galt4 cDNA and concomitantly administering shRNA/siRNA St3gal2 to increase levels of GM1 in the brain and decrease degradation of GM1; wherein the direct administration of GM1 increases GM1 directly and the B3Galt4 cDNA and shRNA/siRNA for St3gal2 provide protective and restorative effects by modulating and increasing the native production of GM1 in the brain.

A further embodiment is a method of increasing the amount of GM1 in a brain tissue comprising a concomitant treatment of a dietary supplement with complex milk lipids (CMLs) having a concentrated dietary source of GM3, to provide increase levels of substrate GM3 and GM2 for conversion to GM1 and gene therapy comprising an AAV or lentivirus encoding for B3Galt4, wherein the CMLs provide increased substrate to convert GM3 and GM2 to GM1 and increased expression of B3Galt4 increases conversion of GM2 to GM1 in the brain. The AAV or lentivirus or non-viral vector is administered to up regulate the production of B3Galt4; and wherein the levels of GM1 in the brain are thereafter increased as compared to the levels prior to administration.

A further embodiment is directed to a composition of matter suitable for increasing GM1 in the brain comprising a vector expressing an exogenous nucleic acid sequence comprising a functional sialidase directed to a Neu3 enzyme, B3Galt4, St3Gal2, or combinations thereof, and a promoter operably linked to said nucleic acid sequence. Said composition can suitably be utilized for treatment of neurodegenerative diseases or disorders to modify the amounts of GM1 in the brain.

A further embodiment is directed to a method for treating a neurodegenerative disease or condition comprising administering an effective amount of a human compatible engineered non-viral vectors including liposomes, polymersomes, lipopolyplex, or bolaamphiphile nanovesicles (that can be targeted to specific neuron subtypes) containing the Neu3 sequence under the control of neuronal specific promoters. The same basic strategies for non-viral vectors are also suitably used for B3Galt4 or St3Gal2 as described herein.

A further method is directed to treating a neurodegenerative disease comprising administering to a patient a human compatible lentivirus encoding for Sialidase Neu3, B3Galt4, or both. Appropriate strategies may employ use of any one of the compositions of matter as a medicament for treating a neurodegenerative disorder or use of said compositions of matter for increasing GM1 in the brain.

A method of increasing the amount of GM1 in a brain tissue comprising a concomitant treatment of a dietary supplement with complex milk lipids (CMLs) having a concentrated dietary source of GM3, to provide increase levels of substrate GM3 and GM2 for conversion to GM1 and gene therapy comprising an AAV encoding for sialidase Neu3, wherein the CMLs provide increased substrate to convert GM3 and GM2 to GM1 in the brain and the AAV is administered to up regulate the production of GM1 through modification of sialidase Neu3 so as to modify and stabilize the levels of GM1 in the brain; and wherein the levels of GM1 in the brain are thereafter increased as compared to the levels prior to administration.

A composition of matter comprising an adeno-associated virus (AAV) or other human compatible virus, encoding the gene for Sialidase Neu3, B3Galt4, St3Gal2, or combinations thereof, and a neuron specific promoter, wherein the composition is suitable for administration to a patient comprising injecting the AAV or other human compatible virus into the brain by intracranial stereotaxic injunction; wherein the AAV's encoding for the Sialidase Neu3, B3Galt4, St3Gal2, or combinations thereof enhance and/or normalize levels of GM1 in neurons, providing both therapeutic relief and disease modifying effects in specific areas of the brain relevant to particular neurodegenerative diseases.

Therefore, there is a need for new methods of treatment of neurodegenerative diseases such as PD and HD, including treatments and mechanisms for regulating or reversing a defect in B3Galt4 expression through administration of B3Galt4 cDNA or for administering a sialidase Neu3 cDNA, or combinations thereof, to increase GM1 in the brain.

Additional features and embodiments will be apparent to one of ordinary skill in the art upon consideration of the following detailed description of preferred embodiments and descriptions of the best mode of carrying out the invention.

DETAILED DESCRIPTION OF THE PREFERRED EMBODIMENTS

Figure 1A:
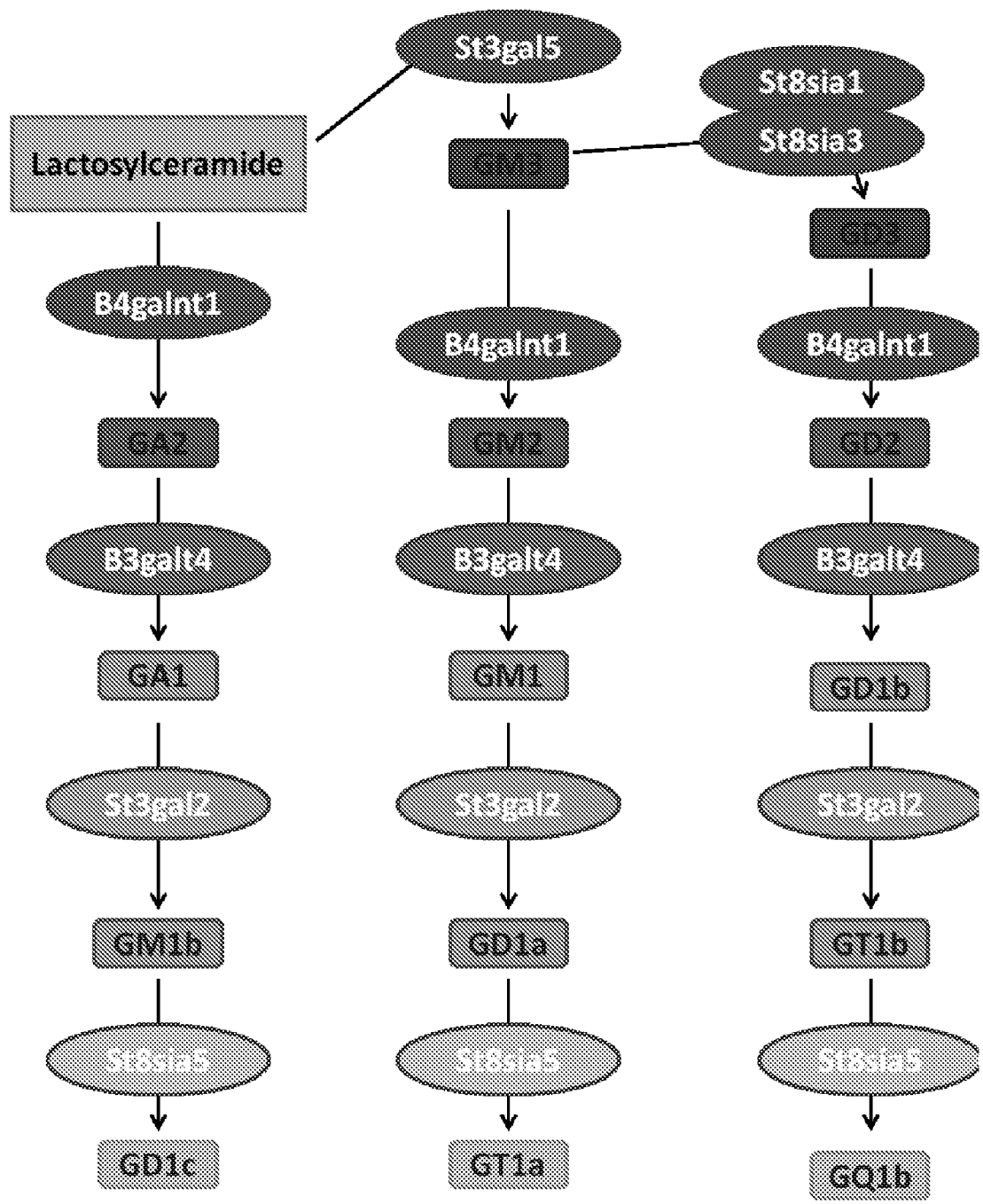
FIGS. 1A-B depicts a flowchart showing ganglioside biosynthetic pathways.

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

The term "increase" is generally used to describe a positive change in the levels of GM1 as compared to pre-treatment levels in the brain.

The term "AAV" means adeno-associated virus.

The term "B3Galt4" means beta-1,3-galactosyltransferase 4 or GM1 synthase.

The term "Sialidase Neu3" means neuraminidase enzyme Neu3.

As used herein, the term "about" means plus or minus 5% of the numerical value of the number with which it is being used. Therefore, about 50% means in the range of 45%-55%.

"Administering" when used in conjunction with a therapeutic means to administer a therapeutic directly to a subject, whereby the agent positively impacts the target. "Administering" a composition may be accomplished by, for example, injection, oral administration, topical administration, or by these methods in combination with other known techniques. Such combination techniques include heating, radiation, ultrasound and the use of delivery agents. When a compound is provided in combination with one or more other active agents (e.g. other anti-atherosclerotic agents such as the class of statins), "administration" and its variants are each understood to include concurrent and sequential provision of the compound or salt and other agents.

By "pharmaceutically acceptable" it is meant the carrier, diluent, adjuvant, or excipient must be compatible with the other ingredients of the formulation and not deleterious to the recipient thereof.

"Composition" as used herein is intended to encompass a product comprising the specified ingredients in the specified amounts, as well as any product which results, directly or indirectly, from combination of the specified ingredients in the specified amounts. Such term in relation to "pharmaceutical composition" is intended to encompass a product comprising the active ingredient(s), and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing the viral or non-viral vectors, cDNA or other delivery vehicles described in the present invention and a pharmaceutically acceptable carrier.

As used herein, the term "agent," "active agent," "therapeutic agent," or "therapeutic" means a compound, composition, or viral or non-viral delivery vehicle utilized to treat, combat, ameliorate, prevent or improve an unwanted condition or disease of a patient. Furthermore, the term "agent," "active agent," "therapeutic agent," or "therapeutic" encompasses a combination of one or more of the compounds of the present invention.

A "therapeutically effective amount" or "effective amount" of a composition is a predetermined amount calculated to achieve the desired effect, i.e., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the compositions of the invention may be used to provide improvement in any of the conditions described. It is also contemplated that the compositions described herein may be administered to healthy subjects or individuals not exhibiting symptoms but who may be at risk of developing a particular disorder. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the chosen dosage ranges are not intended to limit the scope of the invention in any way. A therapeutically effective amount of composition of this invention is typically an amount such that when it is administered in a physiologically tolerable excipient composition, it is sufficient to achieve an effective systemic concentration or local concentration in the tissue depending on the form of administration.

The terms "treat," "treated," or "treating" as used herein refer to both therapeutic treatment and prophylactic or preventative measures, wherein the object is to prevent or slow down (lessen) an undesired physiological condition, disorder, or disease, or to obtain beneficial or desired clinical results. For the purposes of this invention, beneficial or desired results include, but are not limited to, alleviation of symptoms; diminishment of the extent of the condition, disorder, or disease; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease. Treatment includes prolonging survival as compared to expected survival if not receiving treatment.

In various animal models of PD, systemic administration of the a-series ganglioside, GM1, protects dopaminergic (DAergic) neurons from degeneration and restores function to damaged neurons. In a recent clinical trial, administration of GM1 to PD patients resulted in symptomatic improvement and slowed the progression of symptoms. Ganglioside deficiencies and imbalances have been observed in aging and have been suggested to occur in neurodegenerative diseases and these changes may exist in the PD brain. There may be a specific GM1 deficiency and possible decrease in other gangliosides in PD that contributes to neurodegeneration of the nigrostriatal pathway. To explore this possibility, we examined the expression of GM1 (as well as other a- (ex., GD1a) and b- (ex., GD1b and GT1b) series gangliosides) as well as mRNA expression for some of enzymes responsible for ganglioside biosynthesis in the PD brain. We have also examined expression of ganglioside-related genes in dopamine neurons isolated from post mortem PD brain and normal control brain.

The more highly expressed gangliosides in the brain are GM1, GD1a, GD1b, GT1b, and GD3. GD3 is a potential mediator of apoptosis whereas GM1 has been shown to be broadly neuroprotective in a variety of systems and models. Preclinical studies showed that GM1 treatment in various PD models resulted in significant behavioral and biochemical recovery including protection/rescue of damaged dopamine (DA) neurons and increased DA levels in the striatum. A recent randomized, controlled, delayed start clinical study showed that in PD patients, GM1 use for the first 24 weeks of the study was superior to placebo for improving motor symptoms and that extended GM1 use (up to 120 weeks) resulted in a sustained clinical benefit and lower than expected symptom progression. These data suggest that enhancing GM1 levels in PD may be disease modifying. Although GM1 administration has promise as a treatment for PD, it is difficult to source, is currently available only as a natural product extracted and purified from animal brains, and has low ability to cross the blood brain barrier.

The reasons why GM1 treatment is so effective clinically in PD are not completely clear but it is possible that PD is characterized in part by a disorder of glycolipid biosynthesis/metabolism, in particular, a GM1 deficiency disorder, and that GM1 administration represents GM1 replacement therapy. The pathophysiology of the disease may involve alterations in the pathways involved with ganglioside biosynthesis and/or metabolism in the PD brain.

An alternative therapeutic approach to administering GM1 is to increase endogenous GM1 levels in the brain. One method for enhancing GM1 levels in the brain involves the manipulation of ganglioside degradation by sialidases. Sialidases hydrolyze sialic acid linkages on gangliosides and can degrade complex gangliosides (and GD3) while increasing GM1 (where the sialic acid linkage is not susceptible to the sialidase). Specifically, sialidases catalyze the removal of α-linked sialic acid residues from carbohydrate groups of gangliosides. Thus, gangliosides GD1b, GT1b, and GD1a can be converted to GM1 and the potentially apoptogenic GD3 can be degraded.

The human sialidase Neu3 has unique substrate specificity (i.e., degrades complex gangliosides GD1a, GT1b, and GD1b into GM1, does not cleave internal sialic acids on GM1 and GM2, and hydrolyzes GD3) and associates with plasma membranes. Neu3 is active toward plasma membrane gangliosides where it can modify the ganglioside content, specifically increasing GM1 levels and potentially modifying important functional membrane events such as cell signaling. Neu3 also possesses anti-apoptotic properties. Transfection of the Neu3 gene into cancer cells up-regulated Neu3 and inhibited apoptosis, increased Bcl-2 protein, and decreased caspase-3 expression. In contrast, silencing Neu3 expression induced apoptosis without specific stimuli and was accompanied by decreased Bcl-xL (pro-survival protein) expression. Our studies have shown that this process can be stimulated in vivo and it confers neuroprotection in PD models similar to that achieved with administration of GM1.

Indeed, the most highly expressed gangliosides in brain are GM1, GD1a, GD1b, GT1b, and GD3. While GM1 is broadly neuroprotective in a variety of systems and models, GD3 is a potential mediator of apoptosis. The therapeutic method described in this invention will simultaneously decrease GD3 levels (a potential mediator of toxicity) and/or increase GM1 levels (potentially neuroprotective), providing a superior neuroprotective effect. However, any increase in GM1 levels, even without concomitant depreciations in GD3 levels, provides a neuroprotective effect.

In HD models, it has been shown that intracranial administration of bovine brain-derived GM1 resulted in normalized motor function, a concomitant normalization of striatal dopamine levels (critical to normal striatal function), and phosphorylation of mHtt at serine residues 13 and 16 that attenuated mHtt toxicity. These data suggest that enhancing GM1 levels in HD may also be disease modifying.

Therefore, because each of HD and PD exhibit decreases in GM1 ganglioside levels, mechanisms to support GM1 levels or increase GM1 levels will provide protective and stabilizing effects in the brain.

Unfortunately, no drug has yet been developed that has an unequivocal positive effect on disease progression. What is needed is a new treatment for PD that slows the degeneration of substantia nigra dopamine neurons and thus slows, arrests, or reverses the progression of the disease.

GM1 levels can be increased in the brain in several different ways. A first mechanism is to simply administer GM1 to the patient to increase GM1 levels in the affected tissues. This mechanism requires systemic administration of large amounts of GM1 due to the poor ability of GM1 to transport into the brain, has short term benefits of immediate increase of the levels, but suffers from some long term issues, including practical and safety concerns regarding sourcing GM1 from animal brains, the low bioavailability/penetrance of systemically administered GM1 across the blood brain barrier, and no oral bioavailability requiring administration by injection potentially multiple times per day or chronic intracerebral infusion. Therefore, chronic administration of GM1 alone may be difficult and not ideal, based on currently available methods.

Therefore, a preferred embodiment relates to administering a gene therapy designed to increase expression of the human sialidase (neuraminidase) enzyme Neu3, which removes sialic acid residues from complex polysialogangliosides converting them into GM1. Preliminary studies have shown that administration of sialidase enzyme directly to the brain in an animal model of PD has a neuroprotective effect similar to administration of GM1. This mechanism will increase GM1 levels in the targeted tissue (substantia nigra and other brain tissues) and provide a neuroprotective effect similar to that obtained in clinical trials performed in which GM1 was administered to PD patients.

Sialidases, in particular, sialidase Neu3, hydrolyze sialic acid linkages on gangliosides and can degrade complex gangliosides (and GD3) converting them into GM1. Thus, as described above, GD1b, GT1b, and GD1a, are partially converted to GM1 and the potentially apoptogenic GD3 is partially degraded. Thus, application of Neu3 gene therapy will reshape the glycolipid composition of the cell, resulting in a beneficial variation in plasma membrane gangliosides and together with anti-apoptotic effects, will be neuroprotective. Accordingly, the gene therapy encoding for Neu3, provides for a mechanism to partially convert complex polysialogangliosides in the brain into GM1.

The sialidase can be administered via a gene therapy designed to increase expression of GM1 wherein human compatible engineered AAV containing the Sialidase Neu3 sequence under an appropriate promoter is administered. Administration of the AAV is preferentially administered via intracranial stereotaxic injection. In other suitable embodiments, administration of the AAV and the genes encoding for the sialidase Neu3 gene may be administered via other mechanisms known to one of ordinary skill in the art.

Actions of Sialidase

There are a number of different sialidases with somewhat different actions. For example, sialidase C purified from *Clostridium perfringens* (CPS) preferentially cleaves a2-3 linkages, has comparatively little activity at a2-8 linkages and should result primarily in a conversion of GD1a to GM1 (see below). Sialidase V purified from *Vibrio cholerae* (VCS) primarily cleaves a2-8 linkages and terminal a2-3 linkages and should result in a net decrease in GD1a and b-series gangliosides GD1b and GT1b and increased GM1. VCS should also degrade GD3. Therefore, these increases in endogenous GM1 levels (and decreases in potentially damaging GD3 levels) will be neuroprotective against dopamine neuron damage and death from a variety of causes including MPTP/MPP$^+$ mediated DA neuron toxicity as well as DA neuron toxicity mediated by a wide variety of other trigger mechanisms. Indeed, gangliosides GD3, GM3, GD1a and GD1b, but not GM1 or GM2, are good substrates for sialidase Neu3 for increasing endogenous GM1 levels.

Figure 1B:
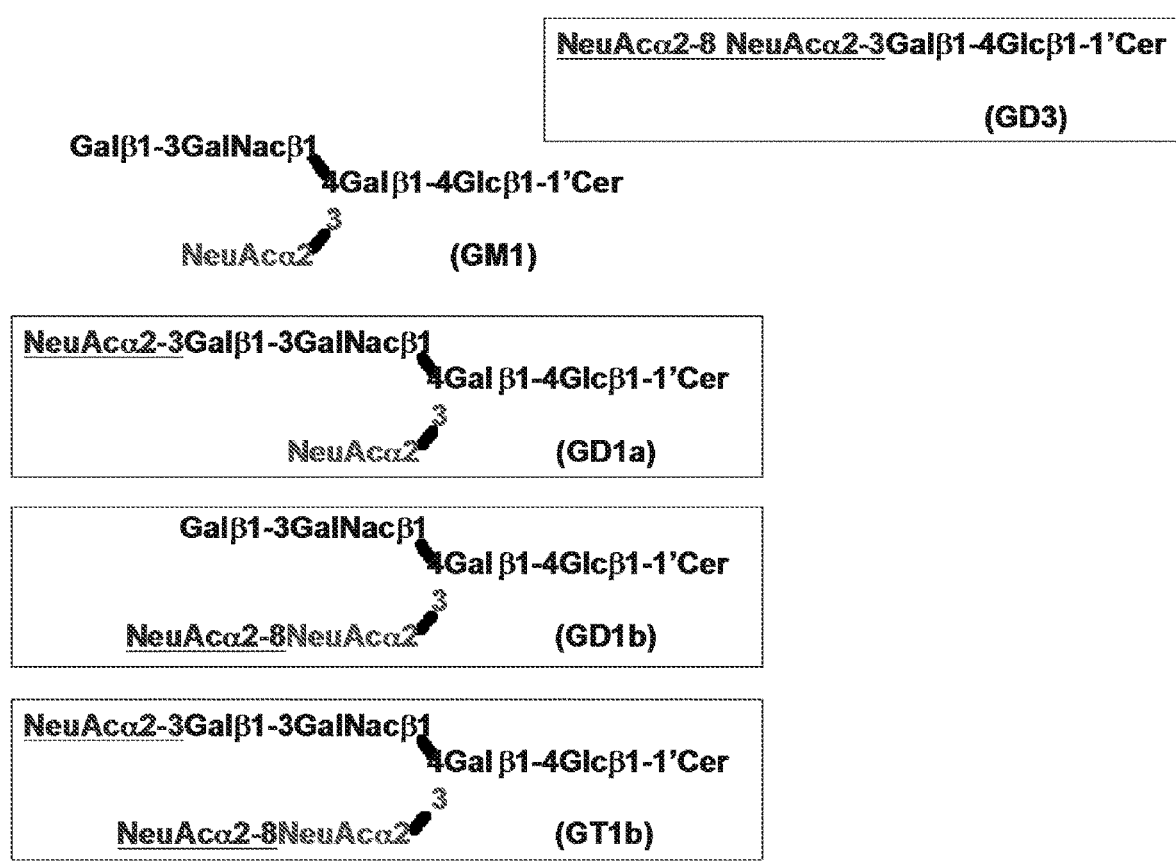

Indeed, FIGS. 1A and 1B depict diagrams of the ganglioside biosynthetic pathways, and depicts several mechanistic ways in which GM1 can be increased through modification of the GM1 biosynthetic pathways. In FIG. 1B, the underlined sialic acids are removed by the action of the sialidase, thus converting those gangliosides into GM1.

Examples

Human Embyonic Stem Cell (hES) Culture:

Human stem cells were differentiated into a dopaminergic (DAergic) phenotype using a well characterized method (Iacovitti et al. 2007 as modified in Cai et al., 2013).

Figure 2:
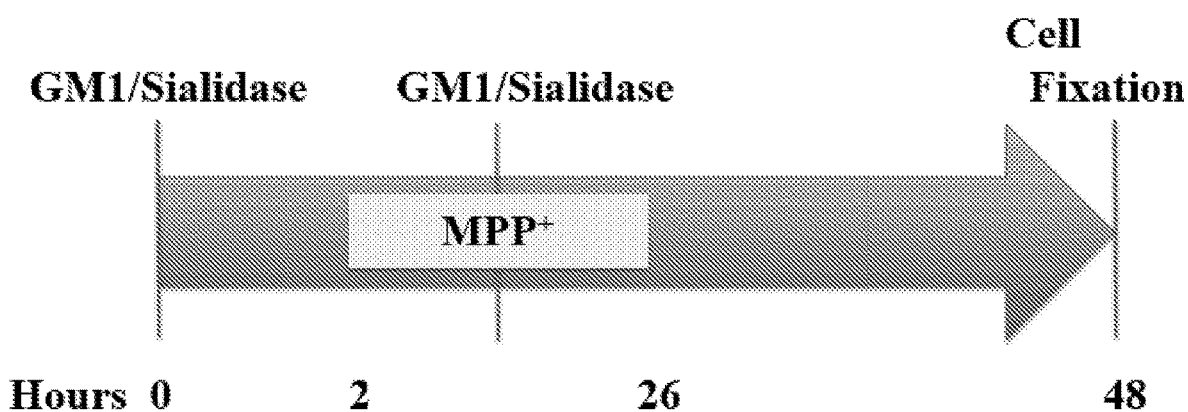
FIG. 2 depicts an experimental overview of hES cells treated with MPP$^+$ and GM1 or sialidase.

FIG. 2 depicts a brief diagram of the experimental overview. Depicted on the top is the material administered and on the bottom is the number of hours.

Rescue of DAergic hES Cells:

hES cells were plated onto 24 well plates. Cells were pretreated with sialidase, GM1 or standard media for 2 hrs and were then exposed to the mitochondrial toxin MPP$^+$. Twenty-four hours later, media containing toxin was removed and fresh media containing the appropriate concentration of rescue agent was added. Two days later, cells were fixed, processed for tyrosine hydroxylase (TH) immunocytochemistry and the number of TH immunopositive cells were counted.

For in vivo studies, sialidases were prepared in artificial cerebral spinal fluid (aCSF) and loaded into Alzet osmotic pumps (model 2004). Brain infusion cannulae were attached to the pumps to allow for intracerebroventricular (ICV) administration of sialidases or vehicle. Brain infusion cannulae were placed in the third ventricle and osmotic pumps were implanted into C57Bl6 male mice (age 7-10 weeks). One week after surgery, sub-acute MPTP administration (2 injections 20 mg/kg s.c. for 5 days) was initiated. Mice were euthanized 2 weeks after the final MPTP injection. In a separate group of animals, GM1 was administered daily (30 mg/kg i.p.) beginning 24 hrs after the final MPTP injection and continuing for two weeks.

Some animals receiving sialidase or aCSF alone were euthanized 12 days post-surgery to examine the effects of sialidase treatment on DA uptake, to examine if sialidase would interfere with DA uptake and inhibit the access of MPTP into DA neurons. Whole striatal homogenates were exposed to [$^3$H] DA for 3 minutes in the presence or absence of mazindol to examine the influence of sialidase treatment on DA uptake.

A the conclusion of the study, the striatum contralateral to the implant was collected to analyze striatal catecholamine and metabolite levels by high performance liquid chromatography (HPLC) according to previously published methods (Kidd and Schneider 2011). Briefly, samples were sonicated in perchloric acid and the soluble fraction was separated using MDTM mobile phase (11% acetonitrile, pH 3.0) on an ESA Coulochem III HPLC system with electrochemical detection.

Sections were cut frozen at 30 μm on a sliding microtome. Every third section through the rostro-caudal extent of the substantia nigra (SN) was processed for TH, the adjacent section was stained with cresyl violet and remaining sections were used for detection of gangliosides. All sections were washed in PBS, (endogenous peroxidase activity was blocked using peroxide for IHC), blocked, and exposed to primary antibody overnight. Sections were then exposed to biotinylated secondary, avidin biotin complex and developed for fluorescence microscopy.

Microbrightfield StereoInvestigator was used to estimate numbers of TH immunopositive and cresyl violet stained cells in the SN by unbiased stereology, as described by us previously (Kidd and Schneider 2011).

Figure 3A:
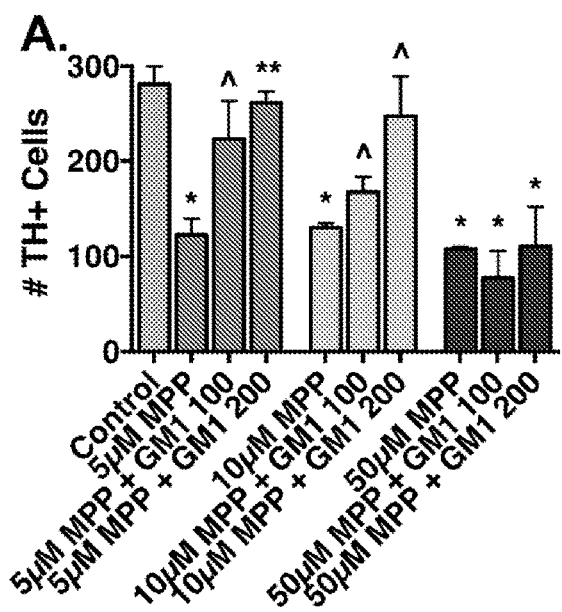
FIGS. 3A and 3B depict the protection/rescue of human embryonic stem cells from MPP$^+$ toxicity.
Figure 3B:
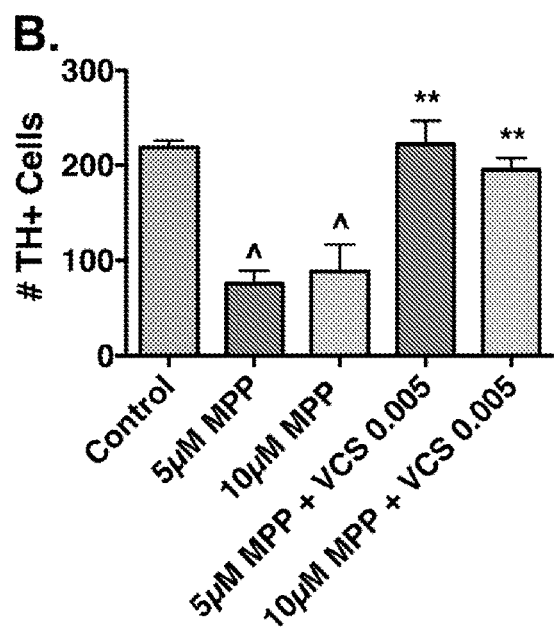

FIGS. 3A and 3B depict the protection/rescue of human embryonic stem cells from MPP$^+$ toxicity. A) The number of tyrosine hydroxylase immunopositive (TH$^+$) cells was reduced as a result of MPP$^+$ treatment. GM1 treatment prevented cell loss at the 5 and 10 μM doses of MPP$^+$. *p<0.01 vs control, ^p<0.05 vs respective MPP$^+$ only, **p<0.01 vs respective MPP$^+$ only. B) Sialidase from *Vibrio cholerae* (VCS) was also able to protect/rescue cells from MPP$^+$ toxicity. ^p<0.01 vs control; **p<0.01 vs respective MPP$^+$ only.

Figure 4:
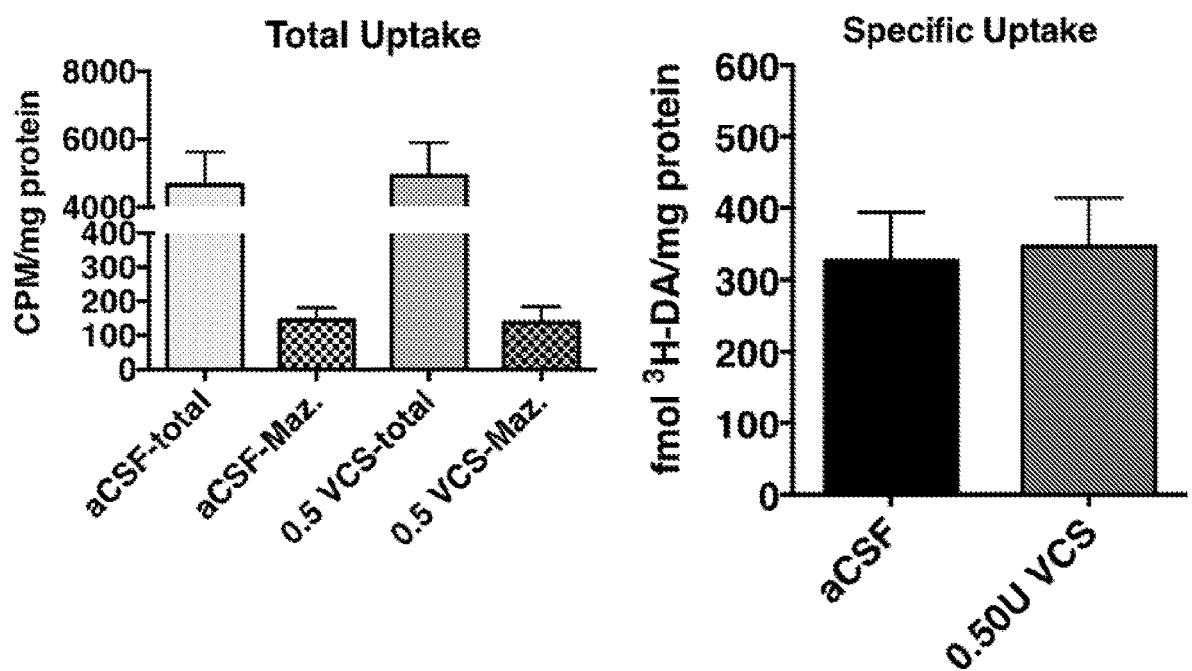
FIG. 4 depicts striatal uptake of tritiated dopamine ($^3$H-DA).
Figure 6A:
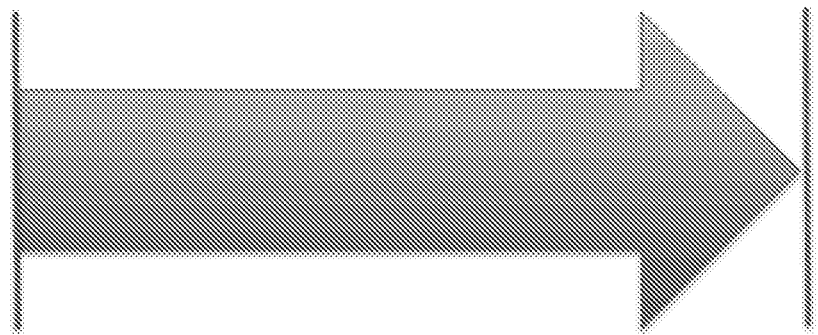
FIGS. 6A and 6B depict experimental overviews of certain mouse studies.

In mouse studies as depicted in FIG. 4, striatal uptake of tritiated dopamine ($^3$H-DA) was examined. FIG. 6A depicts an experimental overview of a dopamine uptake study. Striatal homogenates were incubated with $^3$H-DA in the presence (non-specific) or absence (total) of the DA uptake inhibitor mazindol (Maz). Mazindol effectively blocked total DA uptake; sialidase treatment did not, indicating that the sialidase does not interfere with the mechanism of uptake of MPP$^+$. FIG. 4 further shows that specific uptake of DA in the striatum was not inhibited by intracerebral administration of sialidase to mice for 12 days.

Figure 5:
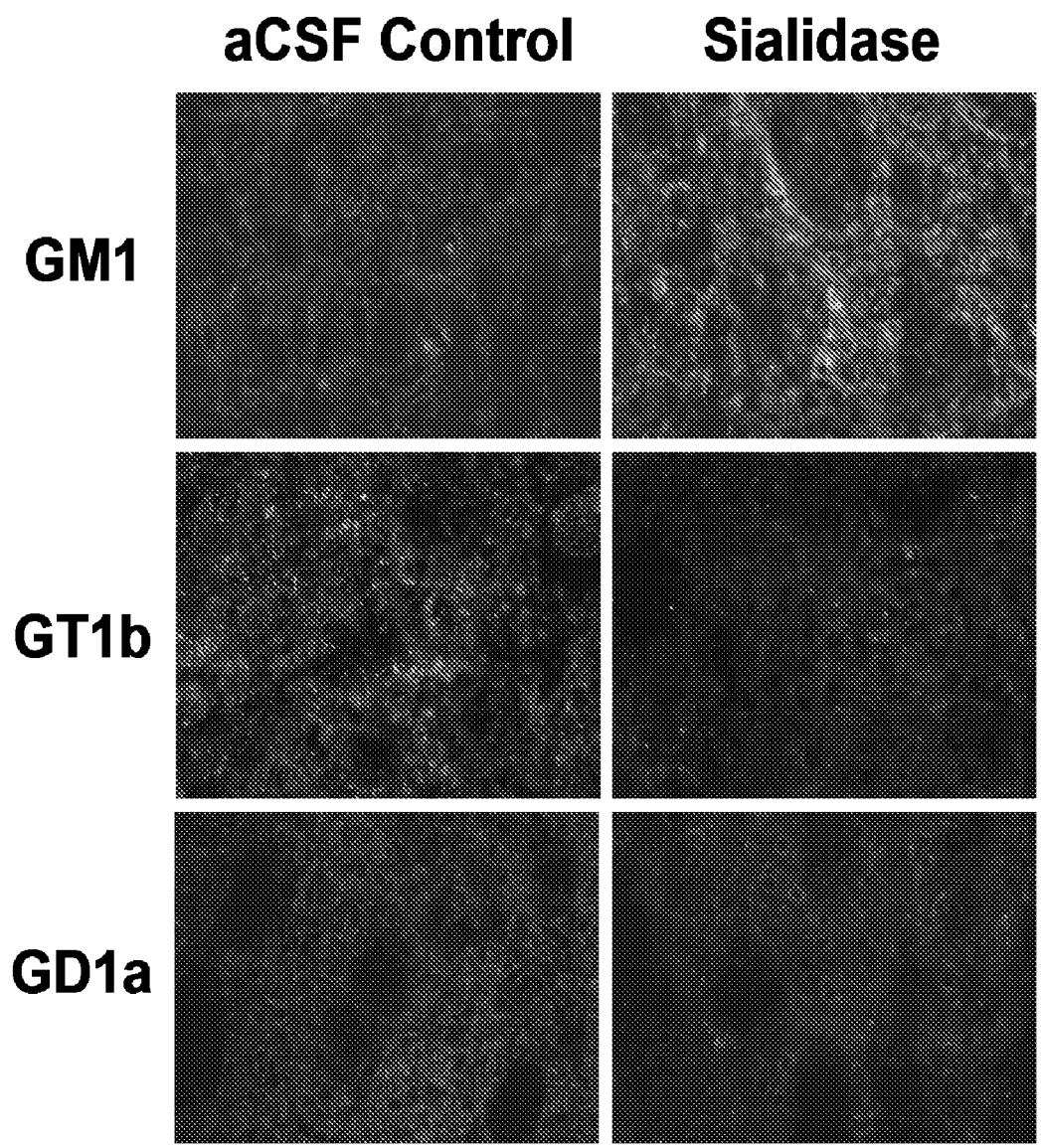
FIG. 5 depicts immunofluorescent detection of gangliosides in mouse brain and effects of sialidase on dopamine levels and number of dopamine neurons.

FIG. 5 depicts immunofluorescent detection of gangliosides in mouse striatum. FIG. 5 depicts striatal sections showing an increase in GM1 and a decrease in GT1b, GD1a, as a result of sialidase treatment.

Figure 6B:
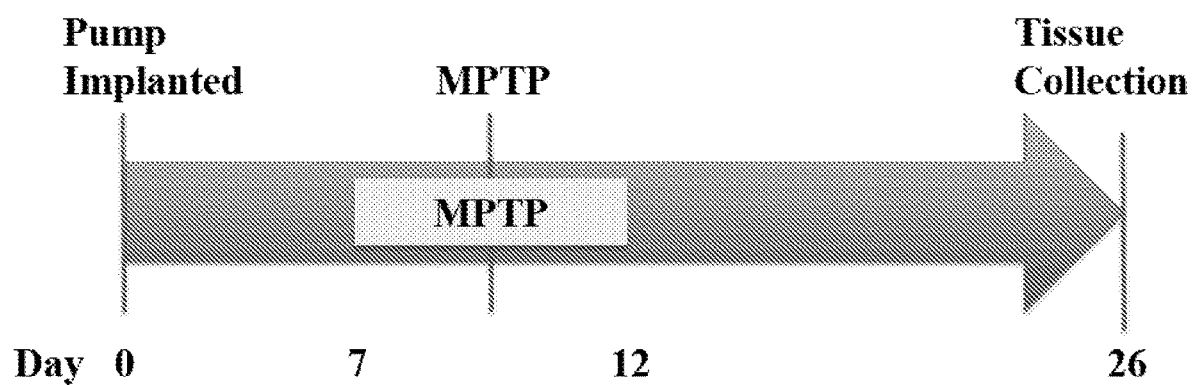
Figure 7:
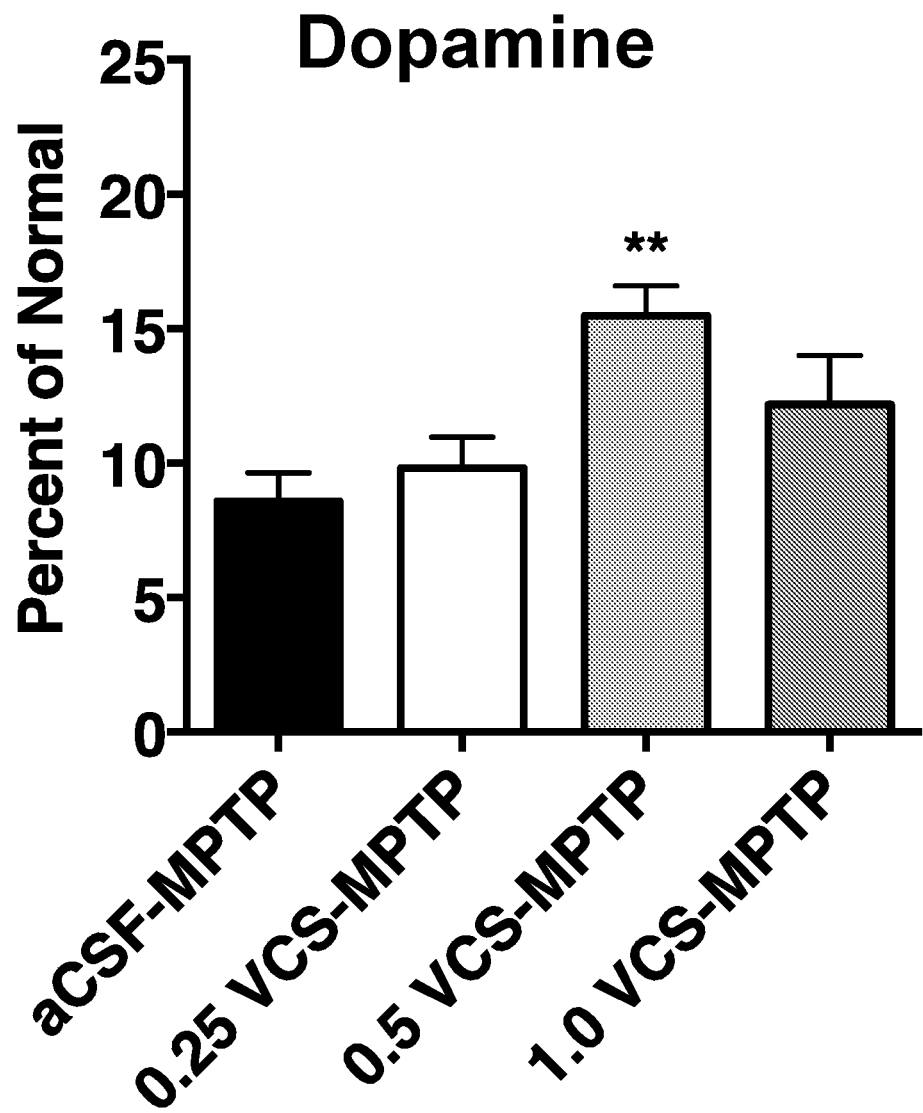
FIG. 7 depicts the effects of sialidase treatment on striatal dopamine levels in a PD model.

FIG. 6B depicts a mouse study from days 0-26 wherein days 7-12 include the animals being subjected to MPTP, the results of which are depicted in FIG. 7.

Figure 8A:
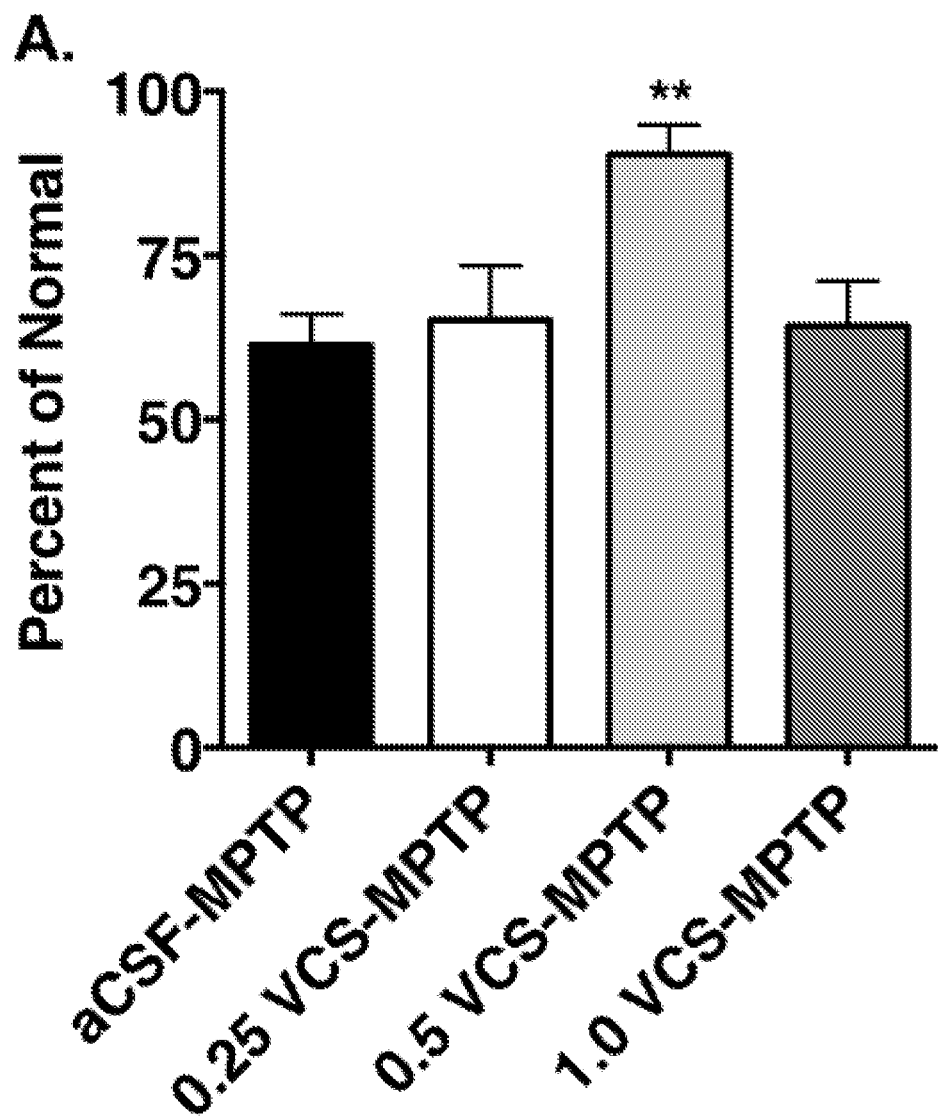
FIGS. 8A, 8B, 8C, and 8D depict the effects of sialidase treatment on substantia nigra neurons in a PD model.
Figure 8B:
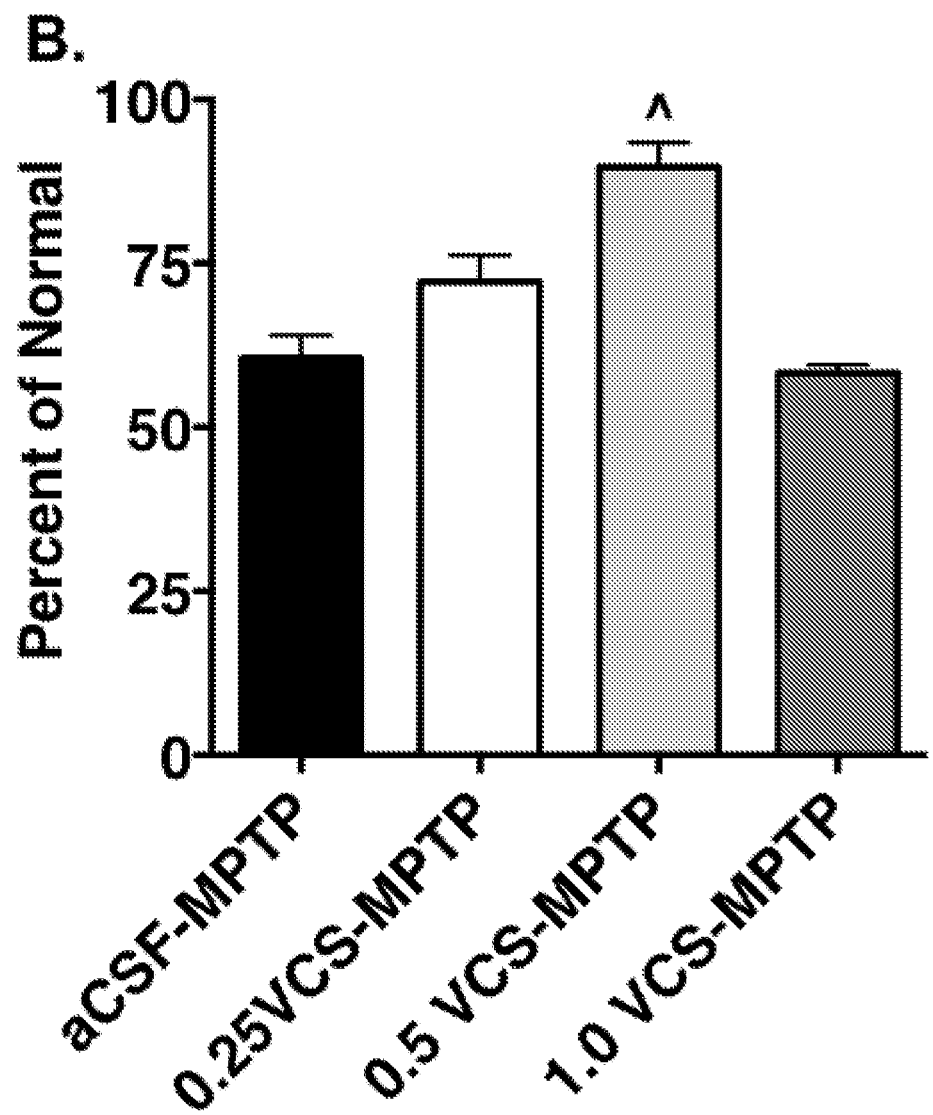
Figure 8C:
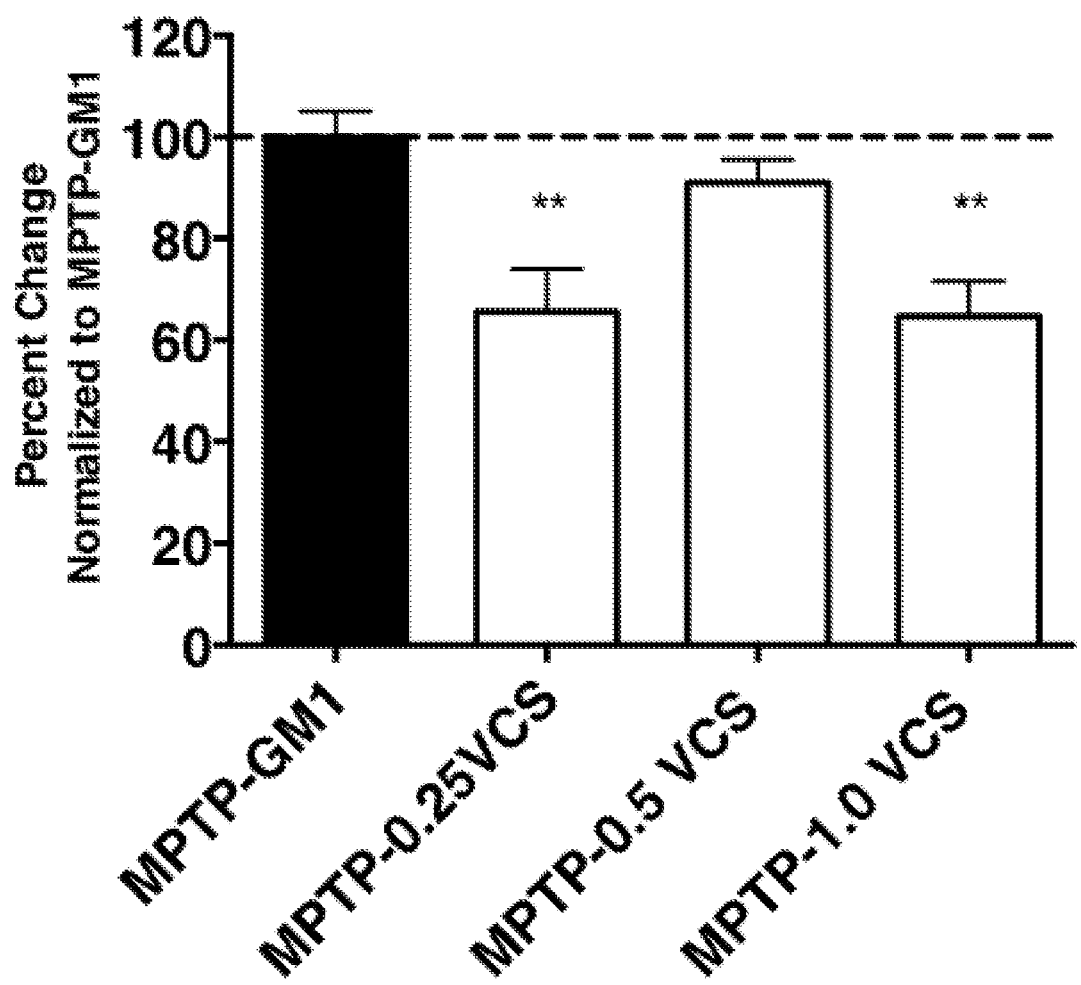
Figure 8D:
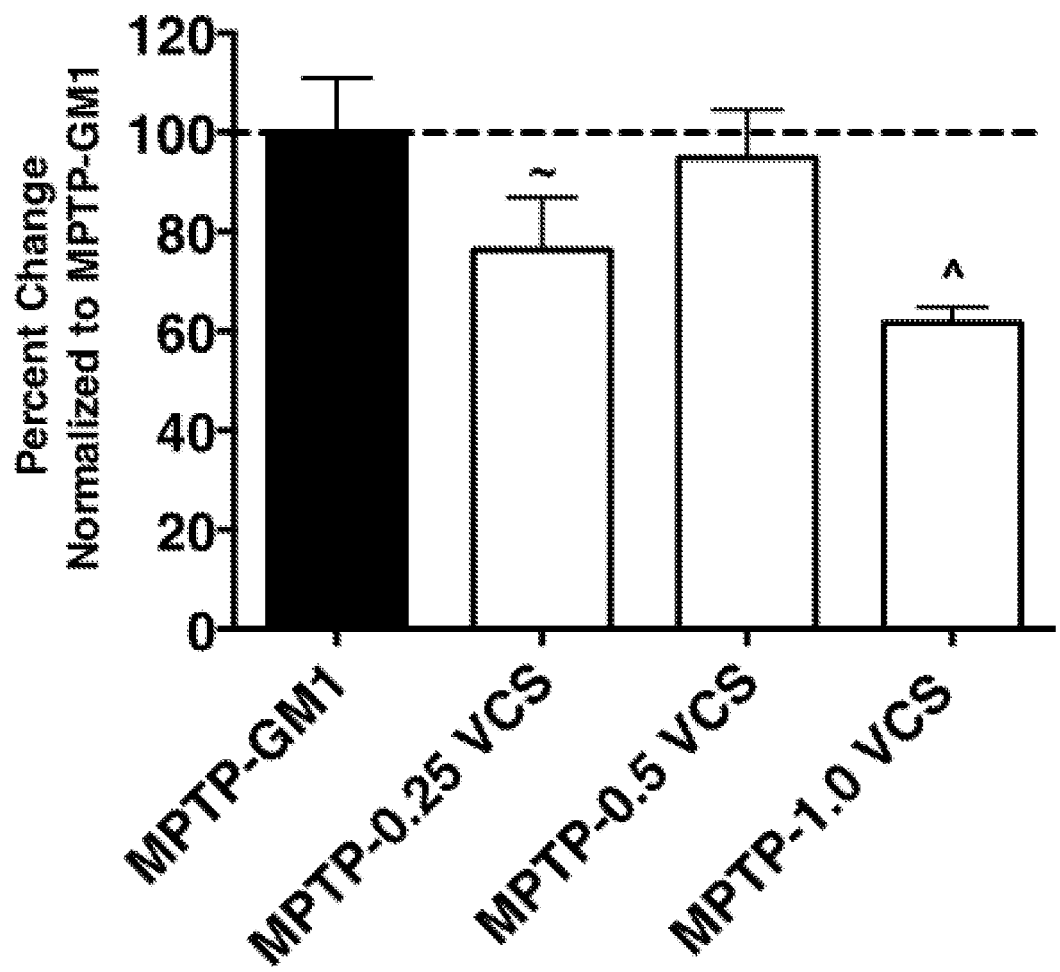

FIG. 7—Effects of sialidase on striatal dopamine levels by HPLC. MPTP treatment resulted in significant decreases in striatal dopamine (DA). In mice that received sialidase infusion for 7 days prior to MPTP and then for an additional 21 days, there was a significant sparing of striatal DA levels compared to animals that received control (aCSF) infusions. p<0.01 vs aCSF-MPTP FIG. 8—Effects of sialidase treatment on substantia nigra (SN) cells. Stereology was used to estimate the number of dopaminergic cells in the substantia nigra. Dopaminergic cells (TH$^+$) with an identifiable nucleus were counted at 100× magnification. Nissl cell counts (number of cresyl violet stained cells) were obtained using the same counting regions of the SN from an individual animal as used in adjacent TH$^+$ sections (FIGS. 8A, 8B: *p<0.01 vs aCSF-MPTP; ^p<0.001 vs aCSF-MPTP). Sub-acute MPTP treatment resulted in significant decreases in TH$^+$ and Nissl-stained cell numbers. GM1 and sialidase treatment had similar protective effects on SN dopamine neurons (FIGS. 8C (TH$^+$ cells), 8D (cresyl violet stained cells): **p<0.001 vs GM1; ^p<0.0001 vs GM1; ~p<0.001 vs GM1).

Figure 9:
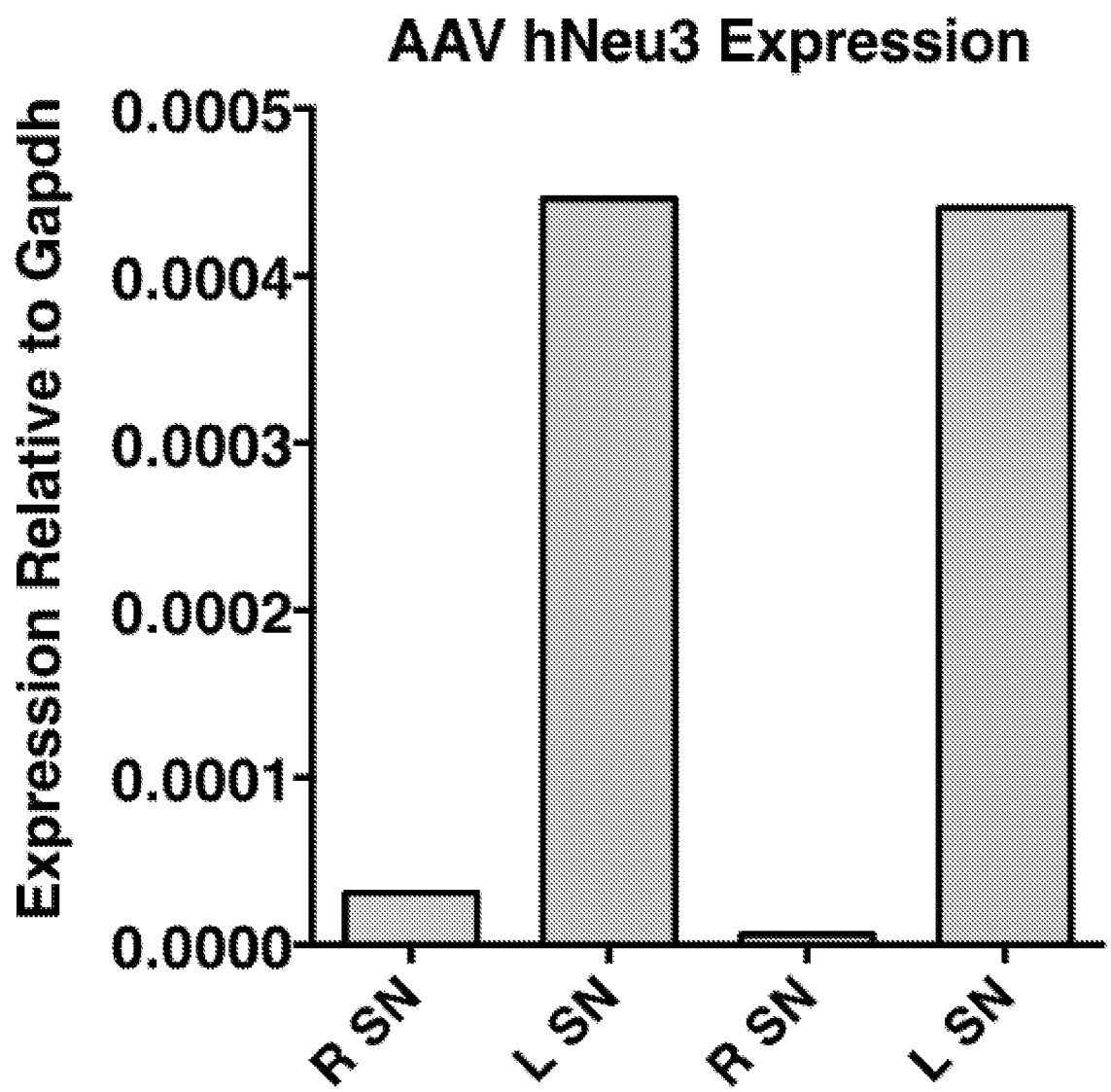
FIG. 9 depicts AAV-hNeu3 expression in mouse substantia nigra 2 weeks after administration.

FIG. 9—AAV-hNeu3 expression in mouse substantia nigra (SN) 2 weeks after administration. An injection of AAV-hNeu3 (1.7×10$^{10}$ GC in 1 μl) was placed just dorsal to the substantia nigra (SN) on one side of the brain. Two weeks later, the animals were euthanized and the SN on each side was dissected and frozen. RNA was extracted from the tissue samples and the samples were run on RT-PCR to assess expression of the hNeu3 transgene.

Figure 10:
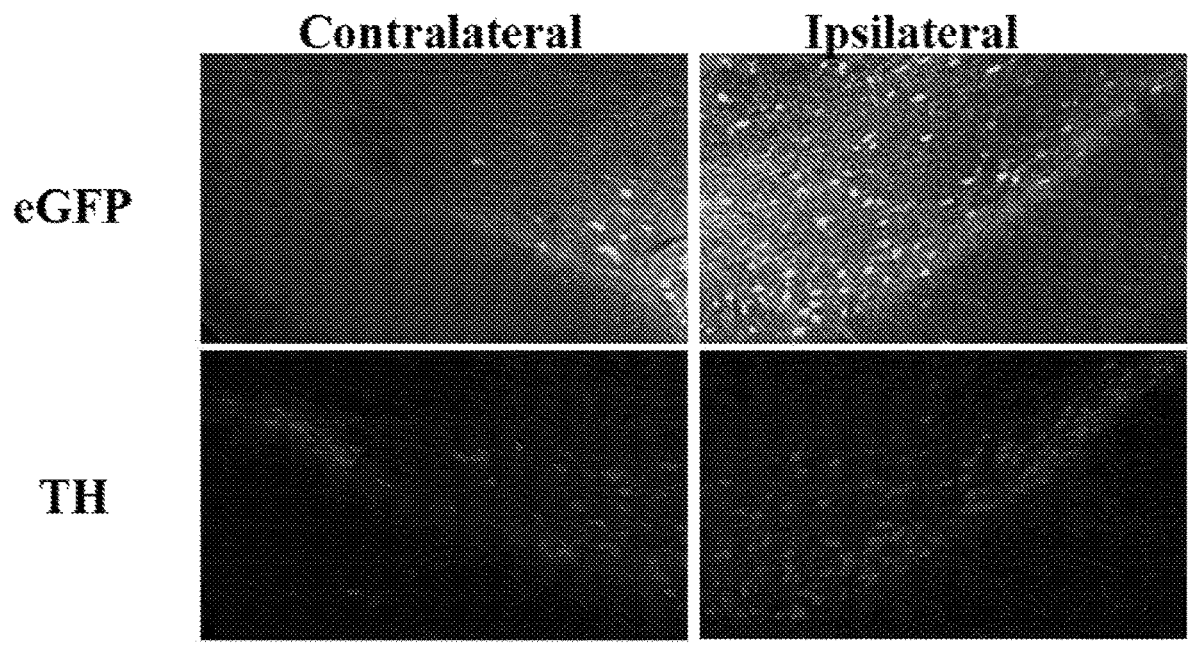
FIG. 10 depicts neuroprotection in an MPTP mouse PD model with AAV-hNeu3 administration.

FIG. 10—Neuroprotection in an MPTP mouse PD model with AAV-hNeu3 administration. AAV-hNeu3 was administered by injection (1.7×10$^{10}$ GC in 1 ul) just dorsal to the substantia nigra (SN) on one side of the brain. Two weeks later, MPTP was administered twice daily for 5 consecutive days. Two weeks after the last MPTP injection, the animals were euthanized by transcardial perfusion and the brains sectioned and labeled for visualization of green fluorescent protein (used as a tag on the AAV to enable localization of the virus in tissue) and tyrosine hydroxylase (to label dopamine neurons). On the side of the brain where AAV-hNeu3 was administered (ipsilateral), there were more dopamine neurons in the SN than compared to the opposite side of the brain that did not receive AAV-hNeu3 (contralateral).

Accordingly, the examples and studies identify that human embryonic stem (hES) cells, when differentiated into dopaminergic neurons, are susceptible to MPP$^+$ toxicity. However, there are mechanisms that exist that can mitigate the effects of MPP$^+$ toxicity. Indeed, MPP$^+$ toxicity in hES cells is mitigated by both GM1 and 0.005 U/mL VCS. Therefore, treatment with a sialidase, such as sialidase Neu3 that increases the amounts of GM1 expression in the striatum and the substantia nigra will provide neuroprotective effects.

Furthermore, the experiments identify that sialidase treatment does not alter MPP$^+$ uptake in vivo and that lack of MPP$^+$ uptake is not the mechanism for neuroprotection from sialidase administration. Conversely, sialidase treatment results in changes in ganglioside expression, resulting in an increase in GM1 expression, in both the striatum and substantia nigra. At least one concentration of sialidase enzyme had a sparing effect on SN dopaminergic neurons. However, an effective amount of sialidase, administered to an animal, provided protective effects in most circumstances. Indeed, some sialidase treatments were as effective as GM1 administration on sparing striatal dopamine levels and SN dopamine neurons.

These data show that increasing endogenous GM1 levels through the use of sialidase enzymes can have significant protective/rescue effects on dopamine neurons, and at least in some instances, to the same extent as administration of GM1 ganglioside. Since GM1 administration is limited based on the difficulty in sourcing the material and on low bioavailability, other suitable materials are important for continuing to learn about and develop mechanisms to otherwise increase GM1 levels in the brain. Therefore, sialidase treatment may be as effective as systemic GM1 administration in sparing striatal DA levels and SN neurons and may be an alternative to systemic GM1 administration as a potential PD disease modifying strategy.

An embodiment comprises a therapeutic treatment comprising a composition of matter such as a pharmaceutical composition comprising a gene therapy vector expressing an exogenous nucleic acid sequence comprising: (1) a nucleic acid sequence encoding a functional Sialidase Neu3 enzyme; (2) a promoter operably linked to said nucleic acid sequence; and (3) wherein the composition of matter is effective at increasing GM1 in the brain.

Indeed, appropriate methods of therapeutic treatment comprising administering the sialidase enzyme to a patient having a neurodegenerative disorder is suitable to prove protective effects through increasing the levels of GM1 in the brain thereby providing protective elements of GM1 and reducing or reversing the course of neurodegenerative disease, such as PD, HD or other known neurodegenerative diseases and conditions that are or may be affected by GM1. In certain embodiments, the sialidase enzyme is appropriately delivered through a composition comprising an AAV encoding for sialidase Neu3. However, other suitable vectors are provided and described herein.

Indeed, it may be further advantageous to provide a therapeutic treatment comprising concomitant administration of GM1 and a gene therapy comprising an AAV encoding for a sialidase enzyme, Neu3, wherein the direct administration of GM1 provides protective effects by increasing GM1 directly and the gene therapy, through increase of sialidase enzyme Neu3 administration can provide mechanistic changes in the brain cells to protective effects through increasing the levels of GM1 in the brain thereby providing protective elements of GM1 and reducing or reversing the course of neurodegenerative disease, such as PD, HD or other known neurodegenerative diseases and conditions that are or may be affected by GM1.

In appropriate settings, the compositions described herein and throughout the embodiments may be advantageously used to treat neurodegenerative diseases or disorders, wherein use of the composition generates an increase in GM1 in the brain. In certain embodiments, use of a composition comprising a viral vector for Sialidase Neu3 as a medicament for treatment of a neurodegenerative disease or disorder is appropriate.

A further therapeutic strategy may utilize the same pathway identified in FIG. 1 but approach the modification or increase of GM1 from a different aspect. In essence, the pathway for GM1 via the arrows depicts a natural flow, wherein GM2 is converted by B3Galt4 into GM1, and GM1 then converted by St3Gal2 into GD1a, or GT1a. The sialidase Neu3 strategy increases GM1 levels by converting the downstream a-series polysialoganglioside GD1a and the b-series polysialogangliosides GD1b and GT1b into GM1. However, a further strategy for increasing GM1 levels would be to increase GM1 directly by correcting a possible defect or error in the production of GM1 from GM2 due to decreased expression of the GM1 synthase enzyme, B3Galt4. This could be achieved through B3Galt4 gene replacement.

Research suggests that in the substantia nigra in the PD brain, and particularly in isolated dopamine neurons, there is a decreased expression of the mRNA for the enzyme B3Galt4 (beta-1,3-galactosyltransferase 4)(AKA GM1 synthase), which contributes to decreased GM1 ganglioside levels in PD substantia nigra, which in turn, supports the degeneration of dopamine neurons. Unfortunately, no drug has yet been developed that unequivocally has a positive effect on disease progression. What is needed is a new treatment for PD that slows the degeneration of substantia nigra dopamine neurons and thus slows, arrests, or reverses the progression of the disease.

In addition to PD and HD, other neurodegenerative diseases such as Alzheimer's disease and ALS also suffer from similar GM1 reduction resulting in damage. Furthermore, several peripheral neuropathies including, but not limited to: diabetic neuropathy, chemotherapy-induced neuropathy such as "chemo-brain," traumatic brain injury, acute spinal cord injury, stroke and retinopathies also may have similar patterns of damage resulting from low GM1 and would benefit from the treatment suggested herein. Alteration in GM1 biosynthesis may be a mechanism common to a wide variety of neurodegenerative disorders that may increase the vulnerability of neurons to degenerating in response to a variety of stressors.

In HD models and in HD fibroblasts, it has been shown that B3Galt4 mRNA is downregulated, resulting in decreased levels of GM1. It has also been shown in HD models that intracranial administration of GM1 resulted in normalized motor function, a concomitant normalization of striatal dopamine levels (critical to normal striatal function), and phosphorylation of mHtt at serine residues 13 and 16 that attenuated mHtt toxicity. These data suggest that enhancing GM1 levels in HD may be disease modifying.

Therefore, because each of HD and PD exhibit decreased GM1 ganglioside levels and defects in B3Galt4 expression, mechanisms to support GM1 levels or increase GM1 levels or correct the B3Galt4 defect will provide protective effects in the brain.

Furthermore, because of the significant impediments to the therapeutic delivery of GM1 in neurodegenerative disease, which include the possible need for chronic intracranial infusion or chronic systemic injection, practical and safety concerns regarding sourcing GM1 from animal brains, low bioavailability/penetrance of systemically administered GM1 across the blood brain barrier, and no oral bioavailability requiring administration by injection potentially multiple times per day or by continuous intracranial infusion, modification or increase of GM1 must be mediated through alternative means.

Accordingly, a more efficient way to increase GM1 levels will be by modifying the cell's own ganglioside biosynthetic capacity utilizing viral or non-viral mediated gene therapy to increase expression of B3Galt4, the enzyme responsible for GM1 synthesis and deficient in PD and HD. Therefore, a preferred embodiment of the invention is particularly related to a method for treating neurodegenerative disease such as PD or HD that is expected to have disease-modifying effects of slowing the progression of the disease comprising increasing the expression of B3Galt4 in the patient.

A preferred mechanism uses administration of a composition comprising GM1 synthase cDNA in an expression vector to increase expression of the enzyme responsible for the direct biosynthesis of GM1. This will increase endogenous levels of GM1 in substantia nigra neurons (in PD) or striatal or cortical neurons (in HD) and leads to the same disease modifying effect as is seen with administration of GM1 ganglioside. This may be achieved alone or in combination with administration of substances intended to increase levels of the precursor(s) for GM1.

Using adeno-associated virus (AAV) encoding these genes under a neuron specific promoter, we will enhance endogenous GM1 expression following a single intracranial administration. A preferred embodiment comprises a composition of matter such as a pharmaceutical composition comprising a gene therapy vector expressing an exogenous nucleic acid sequence comprising: (1) a nucleic acid sequence encoding a functional B3Galt4 enzyme; (2) a promoter operably linked to said nucleic acid sequence; and (3) wherein the composition of matter is effective at increasing GM1 in the brain.

Accordingly, a proposed method comprises modifying the cell's own ganglioside biosynthetic capacity utilizing viral mediated gene therapy to increase expression of B3Galt4. Indeed, a human compatible engineered adeno-associated virus (AAV) containing the B3Galt4 sequence under the control of neuronal specific promoters can be administered to the patient with neurodegenerative disease by intracranial stereotaxic injunction. The AAV's containing the B3Galt4 sequence would then enhance and/or normalize levels of GM1 in neurons, providing both therapeutic relief and disease modifying effects. Furthermore, advances in AAV technologies now provide the potential for systemic administration of AAV's with neuronal targeting in juveniles or adults, allowing for non-surgical treatment of HD in newborns or in at-risk individuals which may further delay/inhibit the occurrence of the disease.

In further embodiments, other forms of gene therapy or other mechanisms of administration are suitable. For example, one of several human compatible viral vectors are suitable for administering the genes of interest. This includes, but is not limited to such viral vectors as lentiviruses. Furthermore, it may be beneficial in certain embodiments to use a lentiviral vector to transmit a B3Galt4 sequence, a sialidase Neu3 sequence, or both to a patient.

In further embodiments non-viral vectors may be used for administering the genes of interest. These include use of liposomes, polymersomes, lipopolyplex, or bolaamphiphile nanovesicles (that can be targeted to specific neuron subtypes). Therefore, certain targeted approaches can be utilized and formulated for specific intra cranial injection or through IV.

In a further embodiment, in conjunction with B3Galt4 gene therapy, the levels of GM1 can be modified through a further pathway wherein the GM1 levels are not upregulated, but the breakdown of GM1 into other gangliosides can be reduced, therefore increasing the levels of GM1. In one pathway, shRNA/siRNA is used to decrease expression of St3gal2 (ST3 beta-galactoside alpha-2,3-sialyltransferase 2 "SIAT4B"). St3gal2 adds sialic acid to the terminal galactose of Gal$\beta$1-3GalNAc-terminated glycolipids, such as GM1 and GD1b, to synthesize GD1a and GT1b. Downregulation of the gene for St3gal2 and inhibition of production of this enzyme results in decreased levels of GD1a and GT1b with a concomitant increase in GM1. This has been shown to occur in St3gal2-null mouse brain (Sturgill et al., 2012).

Therefore, a further proposed embodiment is directed to a composition to increase endogenous GM1 ganglioside levels in the substantia nigra by reversing a defect in B3Galt4 through administration of B3Galt4 cDNA, alone, or in combination with shRNA/siRNA St3gal2, which will further increase GM1 levels, wherein said composition of matter comprises a gene therapy vector expressing an exogeneous nucleic acid sequence comprising: (1) a nucleic acid sequence encoding a functional B3Galt4 enzyme; (2) a promoter operably linked to said nucleic acid sequence; (3) shRNA/siRNA St3gal2; and (4) wherein the composition of matter is effective at increasing GM1 in the brain. Wherein the shRNA/siRNA St3gal2 may be operably linked to the therapeutic vector or provided as a separate medicament and administered concurrently with the therapeutic vector.

Therefore, a further proposed embodiment is directed to a method to increase endogenous GM1 ganglioside levels in the substantia nigra by reversing a defect in B3Galt4 through administration of B3Galt4 cDNA, alone, or in combination with shRNA/siRNA St3gal2, which will further increase GM1 levels.

In treatment of PD, principal administration is direct application of the gene therapy to the substantia nigra. While the treatment is somewhat invasive, PD patients currently receive brain surgery from implantation of deep brain stimulation electrodes. Furthermore, there have been several gene therapy trials in PD including AAV2-GDNF and ProSavin that required surgery. Other suitable routes of administration are discussed throughout this application, wherein the appropriate dose and formulation can be modified by one of ordinary skill in the art.

In certain embodiments, use of a composition comprising a viral vector containing cDNA for B3Galt4 as a medicament for treatment of a neurodegenerative disease or disorder is appropriate. Alternatively, use of a medicament comprising shRNA or siRNA st3gal2 is appropriate for treatment of a neurodegenerative disease or disorder, or use of a combination of medicaments or therapeutics as described herein.

Examples

Tissue:

Post-mortem tissue from PD patients and age matched controls were obtained from the Human Brain and Spinal Fluid Research Center (Los Angeles, Calif.) or the NICHD Brain and Tissue Bank at the University of Maryland.

Fresh frozen tissue was paraffin embedded and sectioned at 10 μm. Sections were briefly fixed in cold 80% acetone prior to neutral red staining prior to laser capture microdissection (LCM). For LCM we used the PixCell II Laser Capture Microdissection instrument (Arcturus Engineering, Mountain View, Calif.). Only DA neurons in the SN with a defined nucleus and containing neuromelanin were sampled. RNA was extracted and RNA amplicon libraries were generated for use with a custom AmpliSeq panel (focused on glycomics and trophic factors) and Next-Gen sequencing using the Ion Personal Genome Machine (PGM) System Quantitative PCR Analysis:

RNA was extracted from fresh frozen samples using the Qiagen miRNeasy kits according to manufacturer's instructions for use on the QIAcube system. Samples were converted to cDNA using the Qiagen Omniscript RT kit and oligo dT primer. Real-Time PCR was performed on cDNA using the Roche LightCycler 480 with Roche LightCycler 480 SYBR Green I Master. 25 ng of cDNA was used per PCR reaction and all samples were analyzed in triplicate. The reaction conditions were as follows: B3galt4-95° C. for 10 minutes and 45 cycles of 95° C. for 15 s and 60° C. for 1 minute. To confirm specificity of amplification the products were subjected to a melting curve analysis at the end of the final annealing period. To analyze the PCR data the $\Delta\Delta C_t$ method was used to calculate fold-regulation of glycosyltransferase mRNA expression relative to B2M (housekeeping gene) expression.

Figure 11:
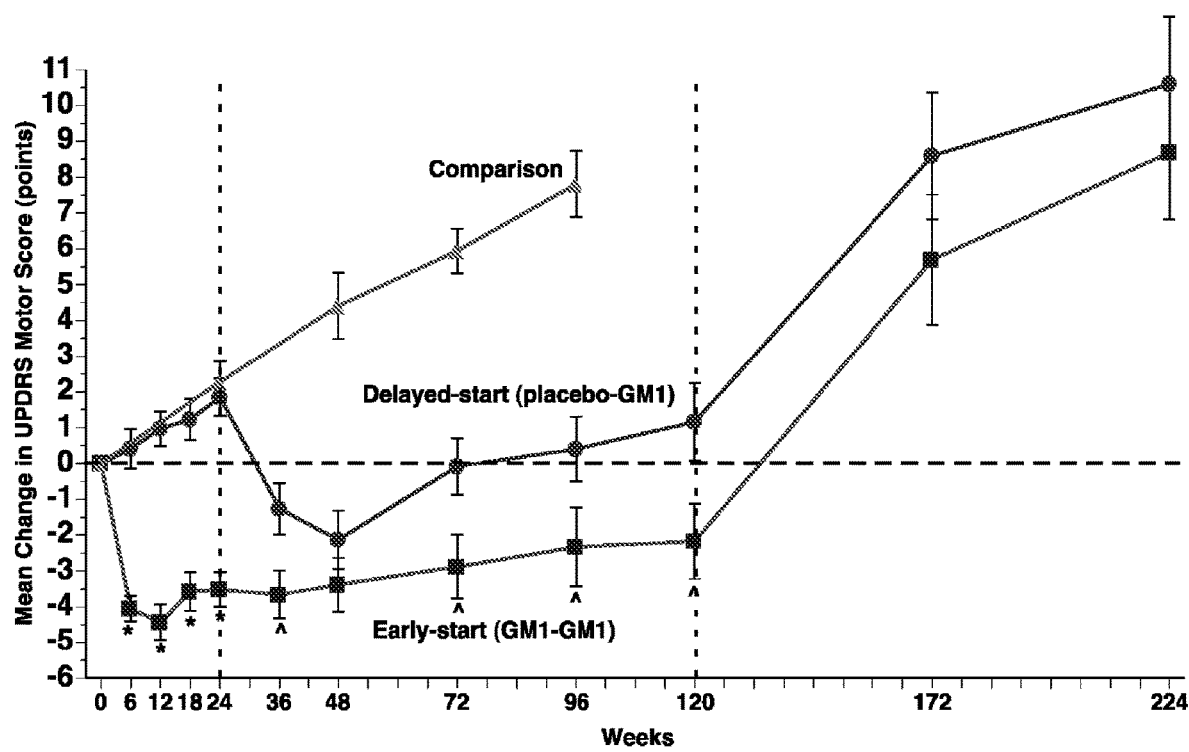
FIG. 11 depicts symptomatic and disease modifying effects of GM1 in PD patients.
Figure 12:
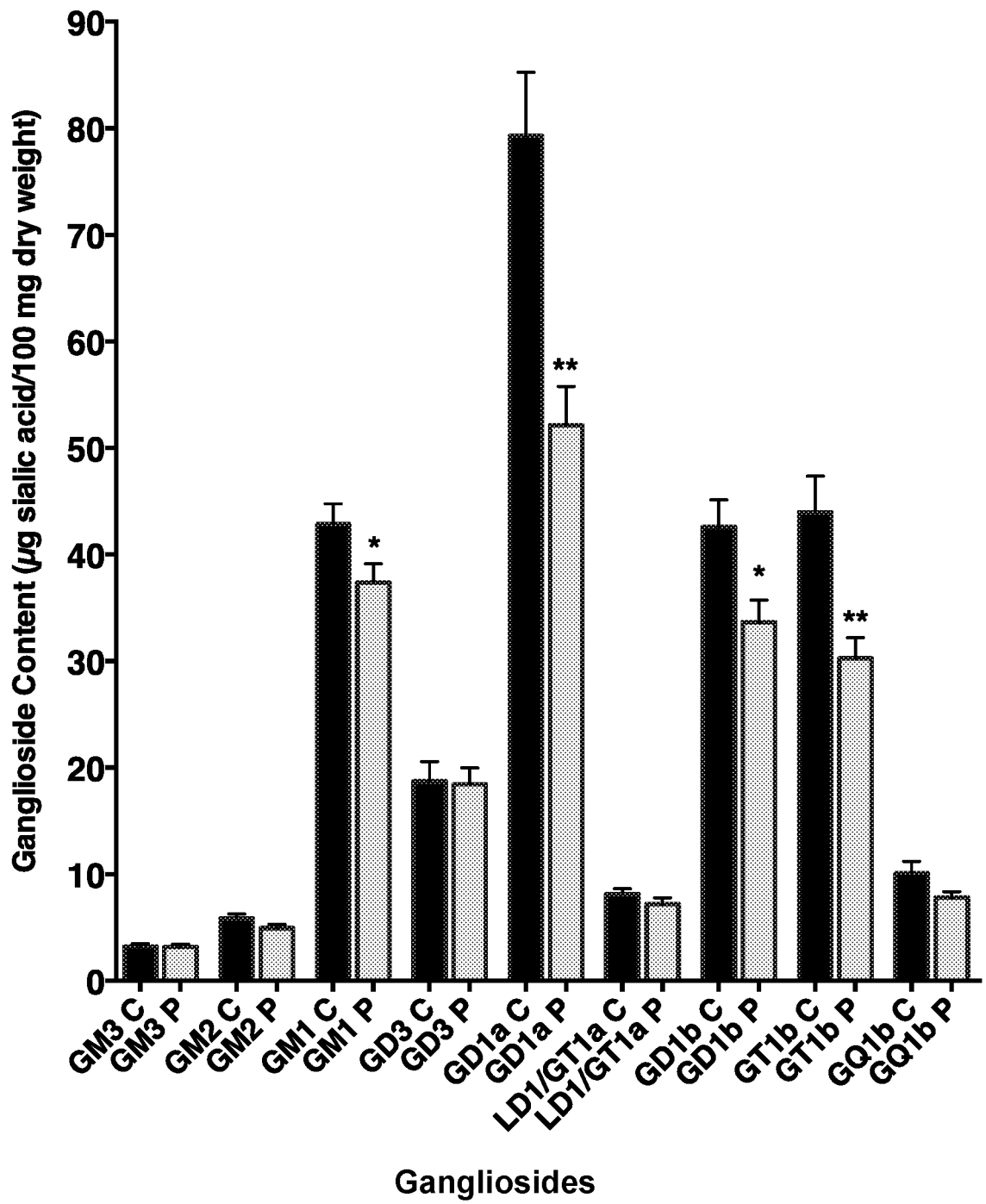
FIG. 12 depicts that some gangliosides are reduced in PD substantia nigra.

FIG. 11—GM1 treatment had an early symptomatic effect and a later disease modifying effect on PD. The mean (±SE) change from baseline in Early-start (randomized to receive GM1 at start of study) and Delayed-start (randomized to receive placebo at start of study) study subjects and in a standard-of-care comparison group (no interventions). The dashed vertical line at week 24 indicates the end of study Phase I. After that, all subjects received GM1. The dashed vertical line at week 120 indicates the end of study Phase II. The horizontal dashed line indicates baseline level. An increase of score indicates symptom worsening; a decrease in score indicates symptom improvement. *=p<0.0001 Early-start vs. Delayed-start; ^=p<0.05 Early-start vs. Delayed-start FIG. 12 depicts that Gangliosides are reduced in Parkinson's disease substantia nigra. Thin layer chromatography data from the SN of 3 PD cases and 4 age-matched controls showing decreased expression of major brain gangliosides GM1, GD1a, GD1b, and GT1b. Therefore, modification of these major brain gangliosides via the mechanisms described herein, leads to neuroprotective effects for patients suffering from theses neurodegenerative diseases.

Figure 13A:
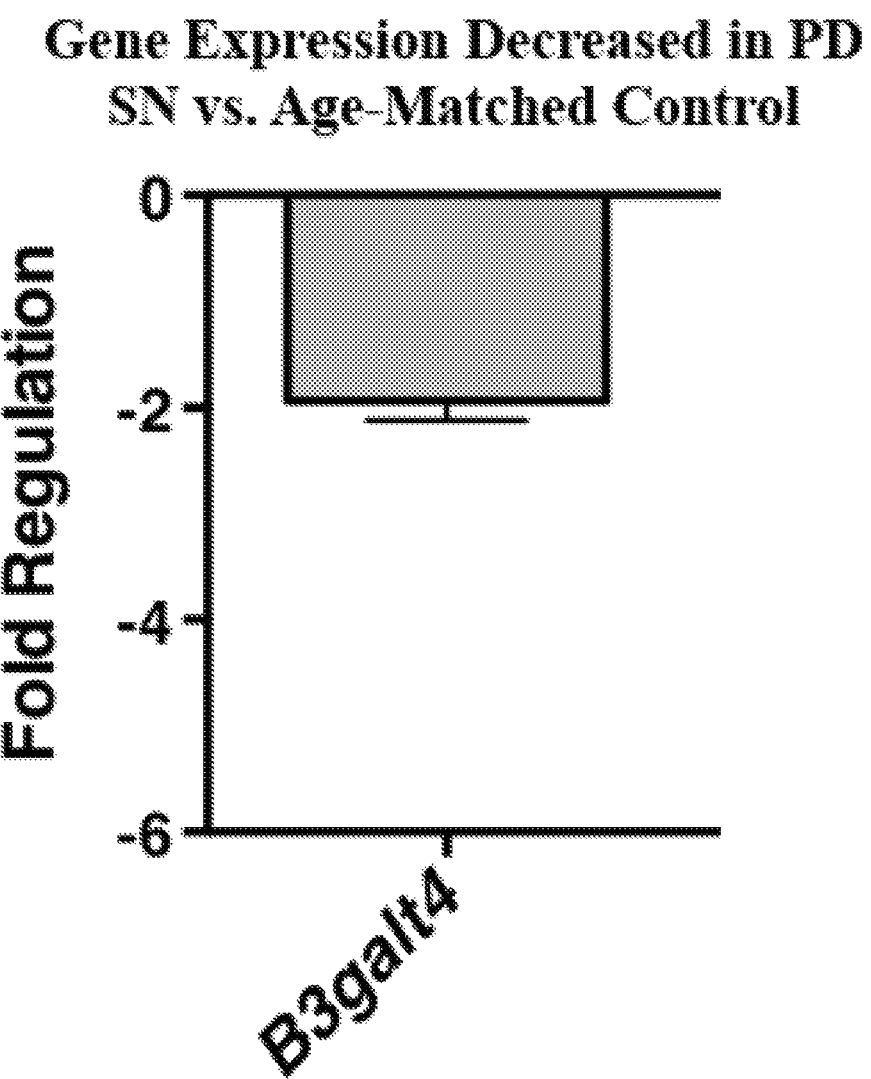
FIG. 13A-B depicts changes in B3Galt4 gene expression SN and decreased B3Galt4 protein expression in human PD substantia nigra.
Figure 13B:
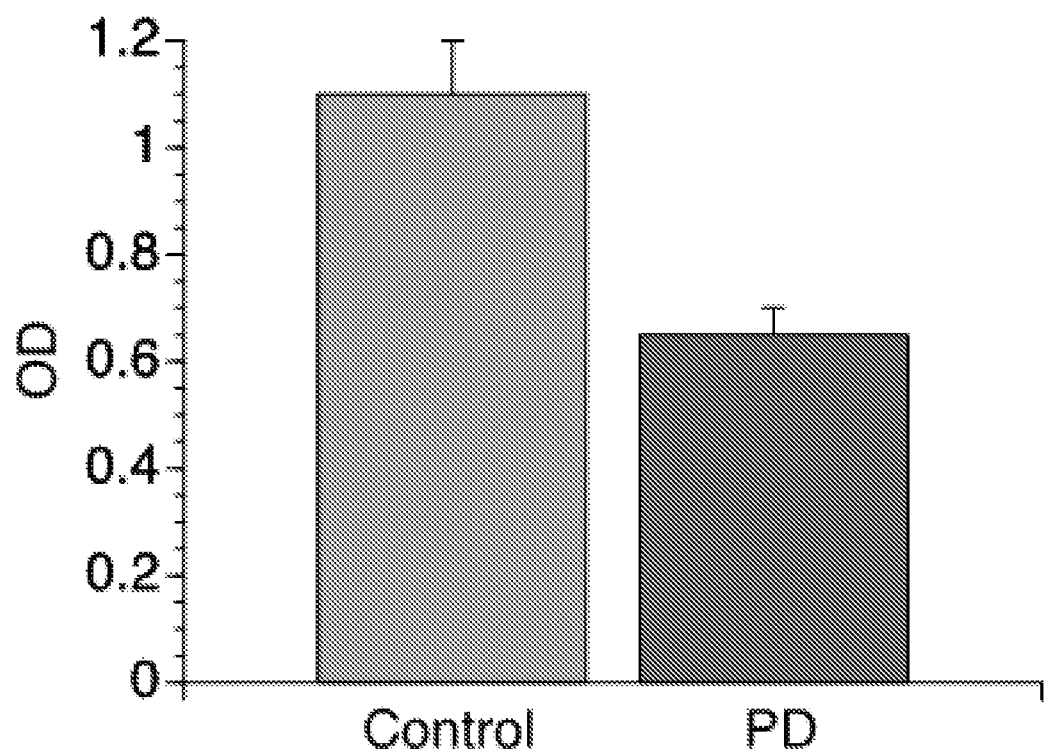

FIGS. 13A and B depict that B3Galt4 gene and protein expression is significantly altered in PD diseased brains. FIG. 13A depicts about a two fold reduction of gene expression in PD brain SN versus age matched control. FIG. 13B further depicts the B3Galt4 Protein Expression in the substantia nigra in PD brain.

Figure 14A:
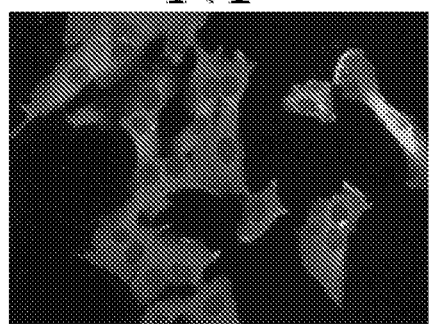
FIG. 14A-B depicts enhancement of cell death when B3Galt4 is downregulated.
Figure 14A:
Figure 14B:
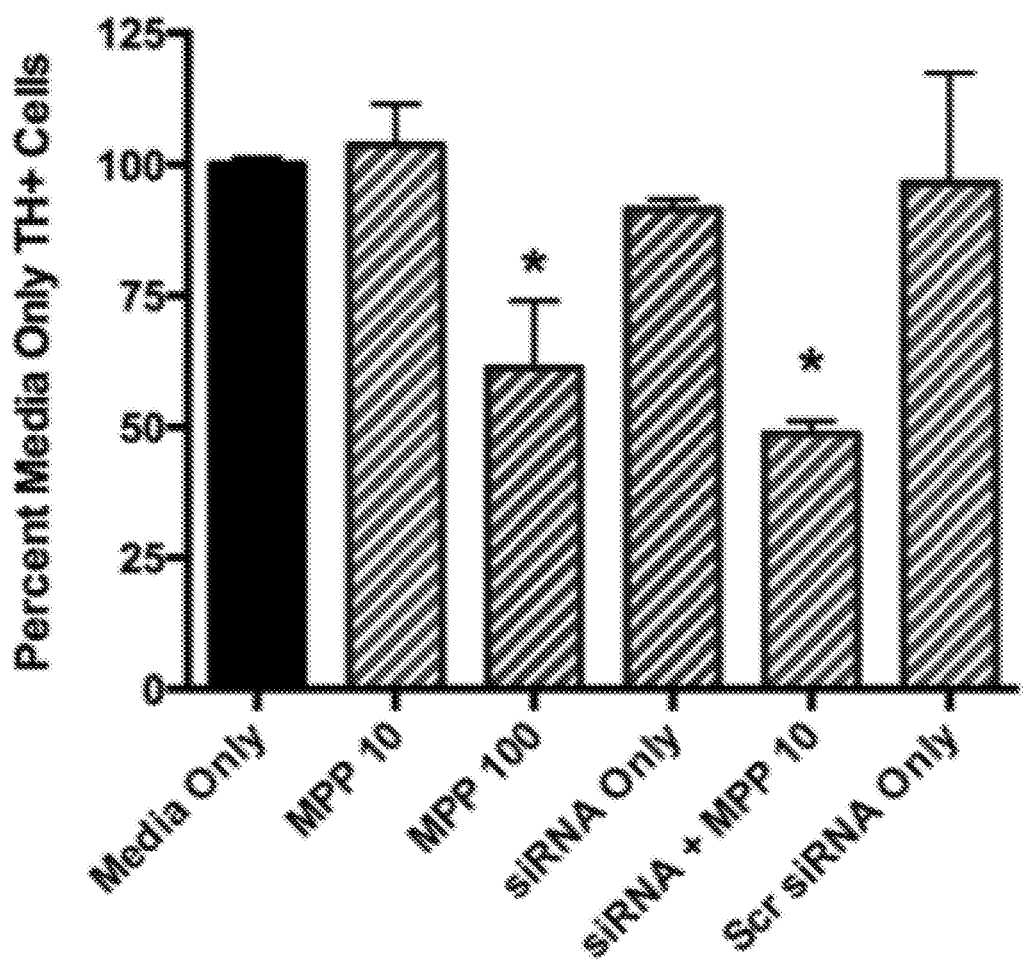

FIGS. 14A and B depict that B3Galt4 siRNA decreases GM1 expression in SK-N-SH Cells. Therefore, and as depicted in FIG. 14B, the downregulation of B3Galt4 results in Enhancement of cell death when B3Galt4 is downregulated. This again leads to the conclusion that appropriate modulation of B3Galt4 can reduce the occurrence of cell death or otherwise stabilize cell death to prevent or slow the progression of disease.

Figure 15A:
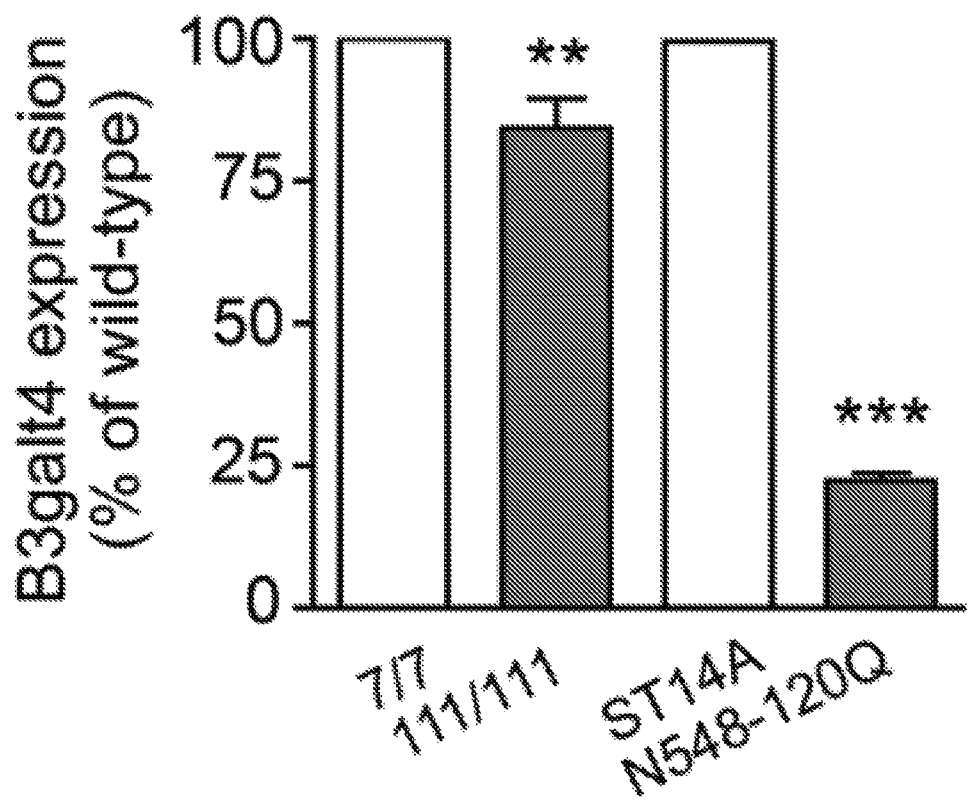
FIG. 15A-B depicts downregulation of B3Galt4 in HID models and HID fibroblasts.
Figure 15B:
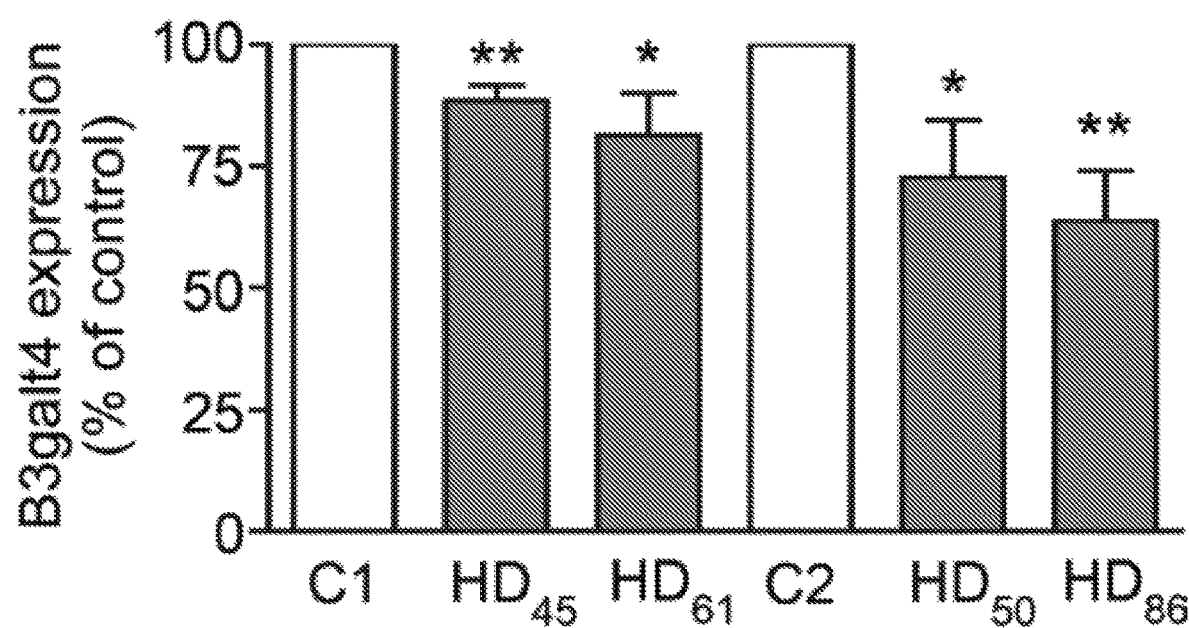

FIGS. 15A and B depict the Downregulation of B3Galt4 in HD models and HD fibroblasts. Therefore, appropriate regulation of B3Galt4, as mediated by the compositions and therapeutic methods or uses of the compositions described herein, can mediate the downregulation of B3Galt4 to reduce the neurodegenerative effects seen in the neurodegenerative diseases.

Figure 16:
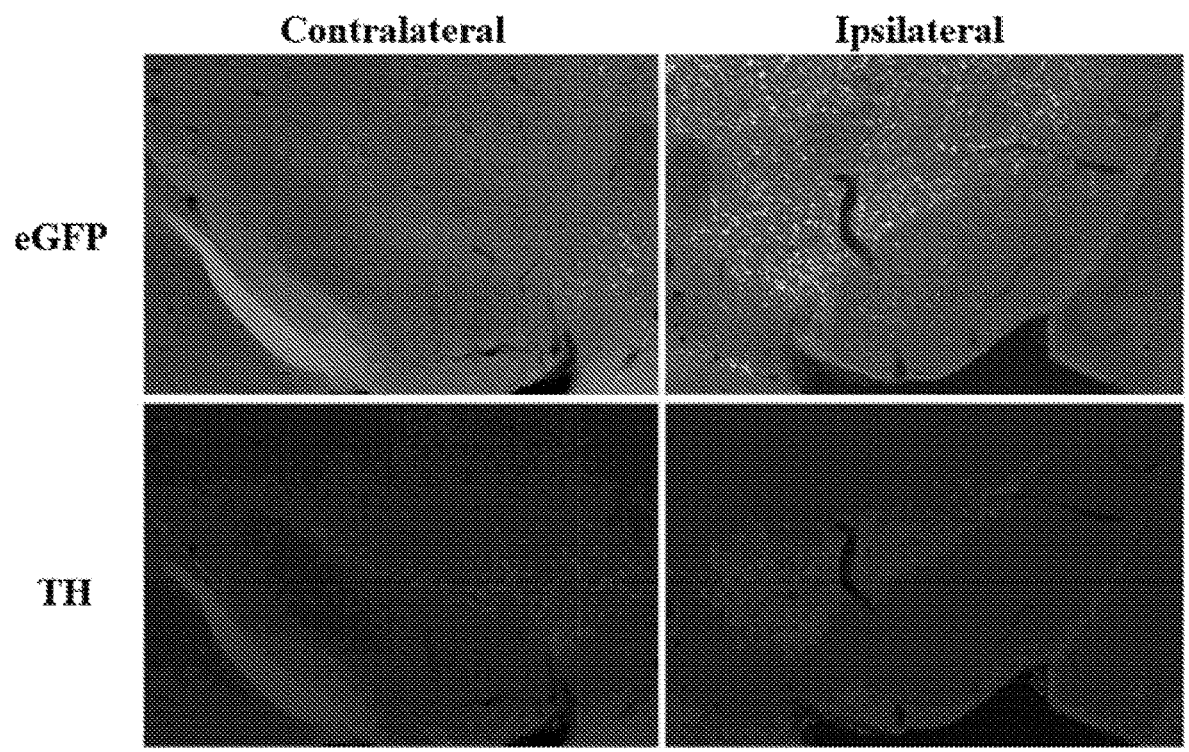
FIG. 16 depicts neuroprotective effect of AAV-B3 Galt4 in the MPTP mouse PD model.

FIG. 16.—depicts side by side images of the contralateral and ipsilateral brain images that identify the significant Neuroprotective effect of AAV-B3Galt4 in the MPTP mouse PD model. The B3Galt4 was administered on just one side of the brain, and wherein the side of the brain where the B3Galt4 was administered, there were more neurons compared to the opposite side of the brain that did not receive the B3Galt4.

GM1 levels appear to be reduced in the substantia nigra of Parkinson's patients even in cells still expressing TH. Glycosyltransferase gene expression is altered in the substantia nigra in Parkinson's patients relative to aged matched controls. Similar gene expression changes also occur in HD brain and in the brain in other neurodegenerative diseases.

Therefore, the present results suggest that there may be a dysregulation of ganglioside biosynthesis in PD (and HD) and that administration of GM1 to PD patients (and in animal and cell models of HD) may provide a clinically important increase in GM1 levels in brain sufficient to overcome a PD (HD)-related GM1 deficit resulting in a neuroprotective/neurorestorative effect.

Because GM1 has proven to have neuroprotective effects in certain neurodegenerative diseases, increase of GM1 proves critical for protecting and improving the life of those who suffer from such diseases. Described herein are several approaches to increasing GM1 in the brain. Where all the strategies may work individually, so to may a combination therapy be relevant for appropriate treatment, and therapies for patients who suffer from these neurodegenerative disorders. Therefore, it is appropriate to generate a combination therapeutic composition that comprises both treatments to correct the B3Galt4 gene and also for increasing the Sialiadase Neu3. Such composition may comprise a single viral or non-viral strategy that includes vectors for each of the strategies, or, a composition may comprise separate vehicles for administering the two different strategies. Furthermore, combined composition may further be administered with additional strategies as described throughout this document.

Further methods may employ two separate compositions administered concurrently in a single medicament, or concurrently in time, with two or more separate compositions or therapeutics administered separately, so that the effects are concurrently seen in the patient.

For example, an embodiment provides for gene therapy, including use of viral vectors containing the sialidase Neu3 sequence of interest. For example, a particular viral vector includes the use of lentiviruses containing the sialidase Neu3 sequence. In certain embodiments, the gene therapy can also include the B3Galt4 sequence alone, or together with sialidase Neu3. In certain embodiments, the gene therapy can also include the St3Gal2 sequence alone, or together with sialidase Neu3. Appropriate viral vectors include lentiviral vectors, retroviruses, adenoviruses, adeno-associated viruses; further more suitable non-viral vectors may also be implemented in certain embodiments.

Therefore, certain embodiments are directed to a concomitant therapy of administering a gene therapy encoding for the human sialidase enzyme Neu3 to increase GM1 levels and decrease GD3 levels in the brain, combined with a gene therapy designed to increase expression of GM1 wherein human compatible engineered AAV containing B3Galt4 sequence under an appropriate promoter is administered via intracranial stereotaxic injection. The combination seeks to increase GM1 production through effects on different GM1 biosynthetic pathways. The B3Galt4 increases low levels of B3Galt4 in PD brain to enhance conversion of GM2 into GM1 (and GD1b from GD2), whereas Neu3, when upregulated through gene therapy, hydrolyzes sialic acid linkages on downstream polysialogangliosides (including GD1b) to partially convert them to GM1 to increase GM1 levels in the brain. The St3Gal2 increases low levels of St3Gal2 in PD brain to enhance conversion of GM1 into GD1a and GD1b into GT1b, whereas Neu3, when upregulated through gene therapy, hydrolyzes sialic acid linkages on GD1a and GT1b to partially convert them to GM1 to increase GM1 levels in the brain.

What is claimed is:

1. A method to increase endogenous GM1 ganglioside in the brain comprising administering B3Galt4 cDNA in an expression vector to increase production of GM1 in the brain.

2. The method of claim 1 further comprising administering GM1 directly to a patient suffering from a neurodegenerative disease, wherein the increase of GM1 ganglioside is targeted in the substantia nigra; wherein the direct administration provides direct increase of GM1 and the B3Galt4 cDNA provides protective and restorative effects by modulating and increasing the native production of GM1 in the brain.

3. The method of claim 1 wherein the increase of GM1 ganglioside is targeted in the caudate and putamen.

4. The expression vector of claim 1 being an AAV.

5. The expression vector of claim 1 being a human compatible virus.

6. The expression vector of claim 1 being a lentivirus.

7. A method for increasing the level of GM1 in the brain comprising:
   a. using an adeno-associated virus (AAV) or other human compatible virus, encoding the gene for B3Galt4 under a neuron specific promoter, and
   b. injecting the AAV or other human compatible virus encoding the gene for B3Galt4 into the brain by intracranial stereotaxic infection; wherein the AAV's encoding the gene for B3Galt4 enhance and/or normalize levels of GM1 in neurons, providing both therapeutic relief and disease modifying effects in specific areas of the brain relevant to particular neurodegenerative diseases.

8. The method of claim 7 wherein the injection is into the substantia nigra.

9. The method of claim 7 wherein the injection is into the caudate nucleus or the caudate nucleus and the putamen.

10. The method of claim 7 wherein the AAV encoding the gene for B3Galt4 is administered systemically.

11. The method of claim 7 further comprising a step of administering a sialidase Neu3 sequence to said patient via an AAV or other human compatible virus.

12. The method of claim 7 further comprising administering an effective amount of purified GM1 ganglioside to said patient.

13. The method of claim 7, further comprising increasing the amount of GM1 in a brain tissue comprising a concomitant treatment of a dietary supplement with complex milk lipids (CMLs) having a concentrated dietary source of GM3, to provide increased levels of substrate GM3 and GM2 for conversion to GM1, wherein the CMLs provide increased substrate to convert GM3 and GM2 to and increased expression of B3Galt4 increases conversion of GM2 to GM1 in the brain.

14. The method of claim 7, further comprising administering to said patient an effective amount of an AAV encoding for St3gal2.

* * * * *